(12) United States Patent
Petruska et al.

(10) Patent No.: US 12,414,937 B2
(45) Date of Patent: Sep. 16, 2025

(54) LOCAL AND REGIONAL ANESTHESIA AND ANALGESIA

(71) Applicant: UNIVERSITY OF LOUISVILLE RESEARCH FOUNDATION, INC., Louisville, KY (US)

(72) Inventors: Jeffrey C. Petruska, Louisville, KY (US); John O. Trent, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 175 days.

(21) Appl. No.: 15/772,609

(22) PCT Filed: Nov. 7, 2016

(86) PCT No.: PCT/US2016/060802
§ 371 (c)(1),
(2) Date: May 1, 2018

(87) PCT Pub. No.: WO2017/079734
PCT Pub. Date: May 11, 2017

(65) Prior Publication Data

US 2020/0383953 A1 Dec. 10, 2020

Related U.S. Application Data

(60) Provisional application No. 62/251,162, filed on Nov. 5, 2015.

(51) Int. Cl.
*A61K 9/00* (2006.01)
*A61K 31/13* (2006.01)
(Continued)

(52) U.S. Cl.
CPC ........ *A61K 31/4174* (2013.01); *A61K 9/0014* (2013.01); *A61K 9/0019* (2013.01);
(Continued)

(58) Field of Classification Search
CPC .......... A61P 23/02; A61P 23/00; A61P 25/00; A61K 9/0019; A61K 3/245;
(Continued)

(56) References Cited

U.S. PATENT DOCUMENTS 4,689,339 A 8/1987 Karjalainen et al.
4,804,539 A 2/1989 Guo et al.
(Continued)

FOREIGN PATENT DOCUMENTS

EP 0183493 6/1986
WO WO-9313074 A1 * 7/1993 ........... C07D 233/64
WO 2003034900 5/2003

OTHER PUBLICATIONS

Mansikka et al. (European Journal of Pharmacology 1995;281:43-48). (Year: 1995).*

(Continued)

*Primary Examiner* — Ernst V Arnold
(74) *Attorney, Agent, or Firm* — Khin K. Chin; Bozicevic, Field & Francis LLP

(57) ABSTRACT

Methods and pharmaceutical compositions are provided, which make use of compounds disclosed herein, including (I). The methods and compositions are useful for producing local or regional anesthesia or analgesia in nerve tissue of a subject.

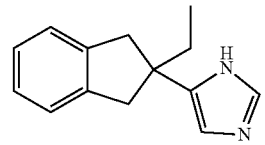

(I)

18 Claims, 6 Drawing Sheets

(51) Int. Cl.
| | |
|---|---|
| A61K 31/137 | (2006.01) |
| A61K 31/196 | (2006.01) |
| A61K 31/245 | (2006.01) |
| A61K 31/4174 | (2006.01) |
| A61K 31/485 | (2006.01) |
| A61K 31/573 | (2006.01) |
| A61K 33/00 | (2006.01) |
| A61K 38/47 | (2006.01) |
| A61K 45/06 | (2006.01) |
| A61P 23/02 | (2006.01) |

(52) U.S. Cl.
CPC .......... *A61K 9/0048* (2013.01); *A61K 31/137* (2013.01); *A61K 31/196* (2013.01); *A61K 31/245* (2013.01); *A61K 31/485* (2013.01); *A61K 31/573* (2013.01); *A61K 33/00* (2013.01); *A61K 38/47* (2013.01); *A61K 45/06* (2013.01); *A61P 23/02* (2018.01)

(58) Field of Classification Search
CPC .............. A61K 31/4174; A61K 9/0014; A61K 9/0048; A61K 31/137; A61K 31/196; A61K 31/245; A61K 31/485; A61K 31/573; A61K 33/00; A61K 38/47; A61K 45/06; A61K 31/4164; C07D 233/58
See application file for complete search history.

(56) References Cited

U.S. PATENT DOCUMENTS

| | | | |
|---|---|---|---|
| 4,883,658 | A | 11/1989 | Holly |
| 4,914,088 | A | 4/1990 | Glonek et al. |
| 5,075,104 | A | 12/1991 | Gressel et al. |
| 5,278,151 | A | 1/1994 | Korb et al. |
| 5,294,607 | A | 3/1994 | Glonek et al. |
| 5,371,108 | A | 12/1994 | Korb et al. |
| 5,498,623 | A | 3/1996 | Karjalainen et al. |
| 5,578,586 | A | 11/1996 | Glonek et al. |
| 6,733,982 | B1 * | 5/2004 | Ford .................... C07D 487/04 435/7.1 |
| 2003/0082225 | A1 | 5/2003 | Mason |
| 2009/0163451 | A1 | 6/2009 | Porreca et al. |
| 2011/0159073 | A1 | 6/2011 | deJuan et al. |

OTHER PUBLICATIONS

Milne et al. (British Journal of Pharmacology 2008; 155:1264-1278) (Year: 2008).*
Gear et al. (Neuroscience 1995;66(1):5-8) (Year: 1995).*
Trescott, A.M. (Pain Physician 2003;6:291-293) (Year: 2003).*
Cleveland Clinic (2001; vol. IV(1):2 pages) and Abelson et al. (Review of Ophthalmology 2009; 3 pages). (Year: 2009).*
Abelson et al. (Review of Ophthalmology 2009; 3 pages) (Year: 2009).*
Kosugi et al. (BJP 2010;160:1662-1676). (Year: 2010).*
Joseph et al. (IEEE Trans Neural Syst Rehabil Eng. Oct. 2011 ; 19(5): 550-557). (Year: 2011).*
Lotfi El Bahri (Pharmacology Compendium May 2008; 30(5): 8 pages). (Year: 2008).*
Lilius et al. (Anesth Analg 2012;114:1353-8) (Year: 2012).*
Kauppila et al. (Pharmacology Biochemistry and Behavior, vol. 59, No. 2, pp. 477-485, 1998) (Year: 1998).*
Becker et al. (2012) "Local Anesthetics: Review of Pharmacological Considerations," *Anesth Prog.* vol. 59, pp. 90-102.
Berlan, M. et al. (2002) "Yohimbine Administration Prevents Over-Responsiveness to Epinephrine Induced by Simulated Microgravity," *Aviat Space Environ Med* 73, 735-742.
Boljka, M. et al. (1994) "Toxic Side Effects of Local Anesthetics on the Human Cornea," *Br J Ophthalmol* 78, 386-389.

Ceresa, B.P. et al. (1994) "Mutation of an Aspartate Residue Highly Conserved Among G-Protein Coupled Receptors Results in Non-reciprocal Disruption of Alpha2a-Adrenergic Receptor-G-Protein Interactions," *J Biol Chem* 272, 12121-12124.
Christoph, T. et al. (2013) "Spinal-Supraspinal and Intrinsic μ-Opioid Receptor Agonist-Norepinephrine Reuptake Inhibitor (MOR-NRI) Synergy of Tapentadol in Diabetic Heat Hyperalgesia in Mice," *J Pharmacol Exp Ther* 347, 794-801.
De Tejada, I.S. et al. (1999) "Design and Evaluation of Nitrosylated -Adrenergic Receptor Antagonists as Potential Agents for the Treatment of Impotence," *J Pharmacol Exp Ther* vol. 290, 121-128.
Fan, S.F. et al. (1992) "F11 Neuroblastoma X DRG Neuron Hybrid Cells Express Inhibitory Mu- and Delta-Opioid Receptors which Increase Voltage-Dependent K+ Currents Upon Activation," *Brain Res* 590, 329-333.
Farley, D.B. et al. (1984) "Quantitation of Alpha 1-Adrenergic Receptors in Porcine Uterine and Mesenteric Arteries," *Am J Obstet Gynecol* 150, pp. 485-491.
Friedenwald, U.S et al. (1944) "Some Factors Concerned in the Mitotic and Wound-Healing Activities of the Corneal Epithelium," *Trans Am Ophthalmol Soc* 42, 371-383.
Grant, R.L. et al. (1994) "Comparative Toxicity of Tetracaine, Proparacaine and Cocaine Evaluated with Primary Cultures of Rabbit Corneal Epithelial Cells," *Exp Eye Res* 58, 469.478.
Habib, A.M. et al. (2015) "Sodium Channels and Pain," *Handb Exp Pharmacol* 227, 39-56.
Huang, J. et al. (2014) "Depolorized Inactivation Overcomes Impaired Activation to Produce DRG Neuron Hyperexcitability in a Nav 1.7 Mutation in a Patient with Distal Limb Pain," *J Neurosci* 34, 12328-12340.
Huang, Y. et al. (1995) "Localization of Alpha 2-Adrenergic Receptor Subtypes in the Anterior Segment of the Human Eye with Selective Antibodies," *Invest Ophthalmol Vis Sci* 36, 2729-2739.
Huuponen, R. et al. (1995) "Buccal Delivery of an Alpha 2-Adrenergic Receptor Antagonist, Atipamezole, in Humans," *Clin Pharmacol Ther* 58, 506-511.
IUPAC-IUB Commission on Biochemical Nomenclature Symbos for Amino-Acid Derivatives and Peptides Recommendations (1971) *Biochem* 11(9):1726-1732.
Jackson, N.M. et al. (2016) "Protein Kinase G Facilitates EGFR-Mediated Cell Death in MDA-MB-468 Cells," *Exp Cell Res.* 346(2):224-232.
Jahnsen, J.A. et al. (2013) "The C-Terminal Half of the Aplha2C-Adrenoceptor Determines the Receptor's Membrane Expression Level and Drug Selectivity," *Naunyn Schmiedebergs Arch Pharmacol* 386, 1031-1040.
Judge, A.J. et al. (1997) "Corneal Endothelial Toxicity of Topical Anesthesia," *Ophthalmology* 104, 1373-1379.
Kadonosono, K. et al. (1998) "Effect of Intracameral Anesthesia on the Corneal Endothelium," *J Cataract Refract Surg* 24, 1377-1381.
Karhuvaara, S. et al. (1990) "Pharmacological Effects and Pharmacokinetics of Atipamezole, a Novel Alpha 2-Adrenoceptor Antagonist-A Randomized, Double-Blind Cross-Over Study in Healthy Male Volunteers," *Br J Clin Pharmacol* 30, 97-106.
Kim, W.J. et al. (1998) "Differences in Keratocyte Apoptosis Following Transepithelial and Laser-Scrape Photorefractive Keratectomy in Rabbits," *J Refract Surg* 14, 526-533.
Koerber, H.R. et al. (1988) "Properties of Somata of Spinal Dorsal Root Ganglion Cells Differ According to Peripheral Receptor Innervated," *J Neurophysiol* 60, 1584-=1596.
Kosugi, T. et al. (2010) "High Concentrations of Dexmedetomidine Inhibit Compound Action Potentials in Frog Sciatic Neres without a2 Adrenoceptor Activation," *British Journal of Pharmacology* 160, 1662-1676.
Leem et al. (2000) Conduction Block by Clonidine is Not Mediated by α2-Adrenergic Receptors in Rat Sciatic Nerve Fibers, Regional Anesthesia and Pain Medicine, *Regional Anesthesia and Pain Medicine* 25(6):620-625.
Lopez De Armentia, M. et al. (2000) "Electrophysiological Properties of Identified Trigeminal Ganglion Neurons Innervating the Cornea of the Mouse," *Neuroscience* 101, 1109-1115.

(56) References Cited

OTHER PUBLICATIONS

Maruta et al. (2011) "Dexmedetomidine and Clonidine Inhibit the Function of Nav 1.7 Independent of α2-Adrenoceptor in Adrenal Chromaffin Cells," *J. Anesth* 25:549-557.
Mc Alvin, J.B. et al. (2015) "Corneal Anesthesia With Site I Sodium Channel Blockers and Dexmedetomidine," *Invest Ophthalmol Vis Sci* 56, 3820-3826.
Meng, I.D. et al. (2015) "Corneal Sensitivity Following Lacrimal Gland Excision in the Rat," *Invest Ophthalmol Vis Sci* 56, 3347-3354.
Park, J. et al. (2013) "Screening Fluorescent Voltage Indicators with Spontaneously Spiking HEK Cells," *PLoS One* 8, e85221.
Peterson, J.L. et al. (2014) "The Role of Endogenous Epidermal Growth Factor Receptor Ligands in Mediating Corneal Epithelial Homeostasis," *Invest Ophthalmol Vis Sci* 55, 2870-2880.
Petruska, J.C et al. (1998) "Anodally Focused Polarization of Peripheral Nerve Allows Discrimination of Myelinated and Unmyelinated Fiber Input to Brainstem Nuclei," *Exp Brain Res* 121:379-390.
Petruska, J.C. et al (2002) "Chemical Responsiveness and Histochemical Phenotype of Electrophysiologically Classified Cells of the Adult Rat Dorsal Root Ganglion," *Neuroscience* 115, 15-30.
Petruska, J.C. et al. (2014) "Organization of Sensory Input to the Nociceptive-Specific Cutaneous Trunk Muscle Reflex in Rat, an Effective Experimental System for Examining Nociception and Plasticity," *J Comp Neurol* 522, 1048-1071.
Rahman, W. et al. (2008) "Peripheral Nerve Injury-Induced Changes in Spinal Alpha(2)-Adrenoceptor-Mediated Modulation of Mechanically Evoked Doral Horn Neuronal Responses," *J Pain* 9, 350-359.
Rau, K.K. et al. (2014) "Distinct Subclassification of DRG Neurons Innervating the Distal Colon and Glans Penis/Distal Urethra Based on the Electrophysiological Current Signature," *J Neurophysiol* 112, 1392-1408.
Rau, K.K. et al. (2016) "Cutaneous Tissue Damage Induces Long-Lasting Nociceptive Sensitization and Regulation of Cellular Stress- and Nerve Injury-Associated Genes in Sensory Neurons," *Exp Neurol* 283, 413-427.
Robin, A.L. (1997) "The Role of Alpha-Agonists in Glaucoma Therapy," *Curr Opin Ophthalmol* 8, 42-49.
Rush, A.M. et al. (2007) "Multiple Sodium Channels and Their Roles in Electrogenesis within Dorsal Root Ganglion Neurons," *J Physiol* 579, 1-14.
Rush, J.S. et al. (2014) "Antagonizing c-Cbl Enhances EGFR-Dependent Corneal Epithelial Homeostasis," *Invest Ophthalmol Vis Sci* 55, 4691-4699.
Sjoholm, B. et al. (1992) "Characterization of [3H}Atipamezole as a Radioligand for Alpha 2-Adrenoceptors," *Eur J Pharmacol* 215, 109-117.
Sjoholm, B. et al. (1995) Nonadrenergic Binding of [3H]Atipamezole in Rat Lung,. A Novel Imidazole Binding Site? *Ann N Y Acad Sci* 763, 66-77.
Sjoholm, B. et al. (1999) "Non-Adrenergic Binding of [3H]Atipamezole in Rat Kidney-Regional Distribution and Comparison to Alpha2-Adrenoceptors," *Br J Pharmacol* 128, 1215-1222.
Stepp, M.A. et al. (1993) "Integrins in the Wounded and Unwounded Stratified Squamous Epithelium of the Cornea," *Invest Ophthalmol Vis Sci* 34, 1829-1844.
Takagi, Y. et al. (2016) "Prospective Observational Post-Marketing Study of Tafluprost 0.0015% Timolol 0.5% Combination Ophthalmic Solution for Glaucoma and Ocular Hypertension: Short-Term Efficacy and Safety," *Ophthalmol Ther*.
Theriault, E. et al. (1988) "Intrinsic Organization of the Rat Cutaneus Trunci Motor Nucleus," *J Neurophysiol* 60, 463-477.
Theriault, E. et al. (1988) "Nociceptive Cutaneous Stimuli Evoke Localized Contractions in a Skeletal Muscle," *J Neurophysiol* 60, 446-462.
Toledano et al. (2009) "Anesthesia Drugs in the Obstetric and Gynecologic Practice," *Reviews in Obstetrics & Gynecology* vol. 2, pp. 93-100.

Wang, S.B. et al. (2012) "Estrogen Negatively Regulates Epithelial Wound Healing and Protective Lipid Mediator Circuits in the Cornea," *FASEB J* 26, 1506-1516.
Wei, H. et al. (2006) "Spinal and Pontine Alpha2-Adrenoceptors Have Opposite Effects on Pain-Related Behavior in the Neuropathic Rat," *Eur J Pharmacol* 551, 41-49.
Wieringa, P. et al. (2012) "Nanotopography Induced Contact Guidance of the F11 Cell Line During Neuronal Differentiation: a Neuronal Model Cell Line for Tissue Scaffold Development," *Nanotechnology* 23, 275102.
Woldemussie, E. et al. (2007) "Localization of Alpha 2 Receptors in Ocular Tissues," *Vis Neurosci* 24, 745-756.
U.S. Patent and Trademark Office, International Search Report and Written Opinion issued in corresponding Application No. PCT/US2016/060802 mailed Nov. 7, 2016, 12 pages.
Adam and Friede (1988) "The number of frog sciatic axons increases continually during body growth"; *Anat Embryol 178*; pp. 537-541.
Baldi and Bucherelli, (2005) "The Inverted "U-Shaped" Dose-Effect Relationships in Learning and Memory: Modulation of Arousal and Consolidation"; *Nonlinearity in Biology, Toxicology, and Medicine*, 3; pp. 9-21.
Brown, et al (1989) "Compartmental and Topographical Distributions of Axons in Nerves to the Amphibian (*Bufo* marinus) Glutaeus Muscle"; *The Journal of Comparative Neurology 284*; pp. 231-241.
Calabrese and Baldwin (1997) "The Dose Determines the Stimulation (and Poison): Development of a Chemical Hormesis Database"; *International Journal of Toxicology*, 16: pp. 545-559.
Calabrese and Baldwin (2001) "U-Shaped Dose-Responses in Biology, Toxicology, and Public Health"; *Annu. Rev. Public Health. 22*; pp. 15-33.
Case Western Reserve University; "Compound Action Potentials: Problems when Testing for Block"; Department of Biomedical Engineering Applied Neural Control: J.T. Mortimer; (Mar. 12, 2022) 3 pages.
Fitzgerald, et al (2020) "The cholinesterase inhibitor donepezil has antidepressant-like properties in the mouse forced swim test"; *Translational Psychiatry 10*:255; pp. 1-13.
Fitzgerald, et al (2021) "Repurposing Cholinesterase Inhibitors as Antidepressants? Dose and Stress-Sensitivity May Be Critical to Opening Possibilities"; *Front. Behav. Neurosci.*, 14; pp. 1-12.
Iyer, Vasudeva G. (1993) Understanding nerve conduction and electromyographic studies; Hand Clinics, 9(2); pp. 273-287.
Joseph and Butera (2011) "High Frequency Stimulation Selectively Blocks Different Types of Fibers in Frog Sciatic Nerve"; *IEEE Trans Neural Syst Rehabil Eng. 19*(5); pp. 550-557.
Karhuvaara, et al (1990) "Pharmacological effects and pharmacokinetics of atipamezole, a novel 0L2-adrenoceptor antagonista arandomized, double-blind cross-over study in healthy male volunteers"; *Br. J. clin. Pharmac. 30*; pp. 97-106.
Karhuvaara, et al (1991) "Rapid reversal of a 2-adrenoceptor agonist effects by atipamezole in human volunteers"; *Br. J. clin. Pharmac. 31*; pp. 160-165.
Kimura, Jun (1984) "Principles and pitfalls of nerve conduction studies"; *Ann Neurol.16*(4); pp. 415-429.
Kobayashi, et al (1993) "C fiber generates a slow Na+ spike in the frog sciatic nerve"; *Neuroscience Letters*, 162; pp. 93-96.
Kumamoto, Eiichi (2020) "Inhibition of Fast Nerve Conduction Produced by Analgesics and Analgesic Adjuvants-Possible Involvement in Pain Alleviation"; *Pharmaceuticals 13*(4); pp. 1-32.
MacLennan, et al (1997) Characterization of $\alpha_2$-adrenoceptors mediating contraction of dog saphenous vein: identity with the human $\alpha_{2A}$ subtype; *British Journal of Pharmacology 121*; pp. 1721-1729.
Magori, et al (2019) "Inhibition by general anesthetic propofol of compound action potentials in the frog sciatic nerve and its chemical structure"; *Naunyn-Schmiedeberg's Archives of Pharmacology 392*; pp. 359-369.
Mann, Michael (2021) "The compound action potential"; *Peripheral Nerves*: Chapter 12; 8 pages.
Maruta, et al. (2011) "Dexmedetomidine and clonidine inhibit the function of Nav1.7 independent of $\alpha_2$-adrenoceptor in adrenal chromaffin cells"; *J Anesth 25*; pp. 549-557.

(56) References Cited

OTHER PUBLICATIONS

Nakamura, et al (2003) "The Critical Role of Concentration for Lidocaine Block of Peripheral Nerve In Vivo"; *Anesthesiology 99*; pp. 1189-1197.
Scheinin, et al (1998) Reversal of the Sedative and Sympatholytic Effects of Dexmedetomidine with a Specific $\alpha_2$-adrenoceptor Antagonist Atipamezole: a Pharmacodynamic and Kinetic Study in Healthy Volunteers; *Anesthesiology*, vol. 89; pp. 574-584.
Scurlock, et al (1978) "The Clinical Character of Local Anesthetics: a Function of Frequency-Dependent Conduction Block"; *Acla anaesth. scand. 22*; pp. 601-608.
Yilmaz-Rastoder, et al (2012) "Effect of Adjuvant Drugs on the Action of Local Anesthetics in Isolated Rat Sciatic Nerves"; *Regional Anesthesia and Pain Medicine*, vol. 37, No. 4; pp. 403-409.
Yoshizawa, et al (2021) "Differences in the antinociceptive effects of serotonin-noradrenaline reuptake inhibitors via sodium channel blockade using the veratrine test in mice"; *Neuroreport*, 32(9); pp. 797-802.
Zhu, et al (2010) "Drosotoxin, a selective inhibitor of tetrodotoxin-resistant sodium channels"; *Biochemical Pharmacology 80*; pp. 1296-1302.
Zuardi, et al (2017) "Inverted U-Shaped Dose-Response Curve of the Anxiolytic Effect of Cannabidiol during Public Speaking in Real Life"; *Front Pharmacol 8*; pp. 1-9.

\* cited by examiner

Local anesthetic structures

Aminoesters

Proparacaine

Articaine

Cocaine

Aminoamides

Lidocaine

Bupivacaine

Ropivacaine

Atipamezole

LOCAL AND REGIONAL ANESTHESIA AND ANALGESIA

RELATED APPLICATIONS

This application claims priority from U.S. Provisional Application Ser. No. 62/251,162 filed Nov. 5, 2015, the entire disclosure of which is incorporated herein by this reference.

GOVERNMENT INTEREST

This invention was made with government support under grant number 1U01HL127518 awarded by the National Institutes of Health. The government has certain rights in the invention.

TECHNICAL FIELD

The presently-disclosed subject matter relates to pharmaceutical compositions and methods for producing local or regional anesthesia and analgesia in a nerve tissue of a subject. In particular, the presently-disclosed subject matter relates to producing local or regional anesthesia and analgesia in a nerve tissue of a subject by administering an effective amount of atipamezole to the subject.

INTRODUCTION

Millions of people experience pain that is persistent for which local anesthetics can offer relief; however, existing local anesthetics have significant safety and toxicity issues. For example, over 160 million people each year experience moderate to severe ocular pain that lasts more than a few days, including some with chronic pain conditions. Many of these have pain which remains in spite of topical/oral NSAIDs and narcotics. Local anesthetics offer full pain-relief, but are not approved for use beyond a few hours because of delayed wound healing and severe risk of corneal degradation.

The eye is protected, in part, by a highly innervated corneal epithelial layer that allows a rapid response to trauma and external agents. However, when there is a trauma, surgical procedure, or pathological condition that disrupts is epithelial layer, the high level of innervation can cause chronic and debilitating pain.

In the absence of viable, long-term treatments to manage ocular pain, patients suffer from a severely diminished quality of life, decreased economic productivity, and are at risk of additional eye disease. The development of drugs that could effectively and safely manage chronic ocular pain would have a significant and positive health, social, and economic impact.

With reference to FIG. 1, currently available local anesthetics fall under two classes amino esters (e.g. proparacaine, articaine, cocaine) and amino amides (e.g. lidocaine, bupivacaine, ropivacaine) (FIG. 1). Local anesthetic agents are drugs that stop the conduction of electrical signals along the nerves/axons of the peripheral nervous system, generally by preventing the flow of ions across the membrane though specific types of channels. The major goal in using local anesthetics is to prevent pain-producing signals from reaching the spinal cord and brain.

These known local anesthetic can be very effective over short periods of time and are useful clinically, e.g., for eye examinations and relatively short ophthalmic procedures. Unfortunately, these drugs are limited by toxicity to the nerve and/or surrounding tissues, by patient allergies, and by pharmacological side-effects or as a direct consequence of the conduction of block—most notably the block of motor signals from reaching muscles, resulting and weakness or paralysis of those muscles. Most ocular anesthetics have devastating effects on the structural integrity of the cell membrane that leads to cytotoxicity and subsequent desquamation (3). The corneal epithelial layer is susceptible to erosions and a slower rate of regeneration. As a result, topical, ocular administration of currently approved drugs is contraindicated for more than 2 hours.

Accordingly, there is a need in the art for improved local and regional anesthetics and analgesics, and improved methods of producing local or regional anesthesia or analgesia, which that avoid the disadvantages of existing drugs.

SUMMARY

The presently-disclosed subject matter includes pharmaceutical compositions and methods for producing local or regional anesthesia or analgesia, which do not have the disadvantages associated with existing drugs and methods.

These compositions and methods make use of compounds that are or are a derivative of a compound that is FDA-approved for veterinary use and has had multiple successful Phase I human clinical trials for other purposes. The compounds are structurally-dissimilar from the 'caine-family of local anesthetics and represent a unique set of anesthetic agents.

The compositions and methods have efficacy, including on human sensory neurons, and also have significantly less toxicity for tissues, such as the cornea. Thus, subjects who could benefit from compositions and methods of the presently-disclosed subject matter include, for example, those with ocular traumas (such as physical, chemical and thermal insult), ocular surgeries (such as keratoplasty or LASIK surgery), corneal erosions as a complication of diabetes or a side effect of certain anti-cancer drugs, and dry eye disease. The compositions and methods also have significantly less toxicity for use in open wounds, where known local anesthetics cannot be used because they are readily absorbed, reaching toxic levels, i.e., elevated risk of over-absorption. Thus, subjects that who could benefit from compositions and methods of the presently-disclosed subject matter include, for example, those with conditions such as trauma, burns, pressure sores, or disease states such as epidermolysis bullosa (EB), or for use in intra-operative lavage (open surgery or closed like with arthroscopic surgery).

Examples of other subjects who could benefit include, but are not limited to, those in the dental, obstetrics, or ambulatory surgery settings.

The presently-disclosed subject matter includes a method of producing anesthesia in a nerve, which involves administering to the nerve an effective amount of a compound, or a pharmaceutically-acceptable salt thereof, selected from the group set forth in Table A herein below. In some embodiments, the nerve is in a subject.

The presently-disclosed subject matter further includes a method of producing local or regional anesthesia or analgesia in nerve tissue of a subject, which involves administering to the subject an effective amount a compound, or a pharmaceutically-acceptable salt thereof, selected from the group set forth in Table A. In some embodiments of the methods, the compound is

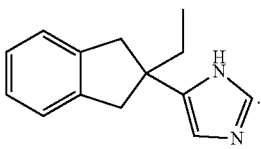 [SMILES: CCC1(c2cnc[nH]2)Cc2ccccc2C1]

In some embodiments, the method also involves identifying the subject as having a need for local anesthesia or analgesia.

In some embodiments, the method also involves identifying the subject as being in need of treatment for a condition selected from the group consisting of neuropathic, inflammatory, post-surgical, trauma-induced, visceral distension-induced, neurodegenerative, cancer-induced, and tissue degeneration-induced, pain or dysesthesia.

In some embodiments, the method also involves identifying the subject as having a resistance or an allergy an amino ester and/or an amino amide local anesthetic.

In some embodiments, the method involves the resistance or allergy is to an amino ester local anesthetic, and the subject has a liver disease. In some embodiments, the method involves resistance or allergy is to an amino amide local anesthetic, and the subject has atypical plasma pseudocholinesterase.

In some embodiments of the method, the subject is in need of a level of retained motor function.

In some embodiments of the method, the subject is a dental patient. In some embodiments of the method, the compound is administered prior to a dental procedure.

In some embodiments of the method, the subject is an obstetric patient. In some embodiments of the method, the compound is administered during labor.

In some embodiments of the method, the subject is has ocular pain. In some embodiments of the method, the subject is in need of treatment associated with ocular trauma, ocular surgery, corneal erosions, or dry eye disease.

In some embodiments of the method, the subject has an open wound. In some embodiments of the method, the compound is administered to the open wound.

In some embodiments of the method, the subject has a condition selected from the group consisting of: trauma, burn, pressure sore, and epidermolysis bullosa (EB). In some embodiments of the method, the subject is undergoing intraoperative lavage. In some embodiments of the method, the compound is administered to an open wound.

In some embodiments of the method, the subject is an animal and the compound is administered prior to a procedure. In some embodiments of the method, the procedure is a procedure for which the animal will be administered general sedation. In some embodiments of the method, the general sedation is not an alpha-2-adrenergic based sedation.

In some embodiments, the method also involves administering a second anesthetic. In some embodiments of the method, the second anesthetic is an amino ester. In some embodiments of the method, the amino ester is selected from the group consisting of: Benzocaine, Chloroprocaine, Cocaine, Cyclomethycaine, Dimethocaine/Larocaine, Piperocaine, Propoxycaine, Procaine (Novocaine), Proparacaine, and Tetracaine (Amethocaine). In some embodiments of the method, the second anesthetic is an amino amide. In some embodiments, the method also involves administering an amino amide. In some embodiments of the method, the amino amide is selected from the group consisting of: Articaine, Bupivacaine, Cinchocaine (Dibucaine), Etidocaine, Levobupivacaine, Lidocaine (Lignocaine), Mepivacaine, Prilocaine, Ropivacaine, and Trimecaine. In some embodiments, the administration of the compound together with the second anesthetic, selected from an amino ester and an amino amide, produces a synergistic effect.

In some embodiments, the method also involves administering an adjuvant, which is not an alpha-2 adjuvant. In some embodiments, the adjuvant is not an alpha-2 adjuvant and the compound is:

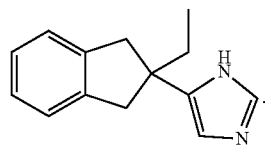 [SMILES: CCC1(c2cnc[nH]2)Cc2ccccc2C1]

In some embodiments of the method, the adjuvant is selected from epinephrine, narcotics, buprenorphine, muscle relaxants, non-steroidal anti-inflammatories, hyaluronidase, bicarbonate, and dexamethasone.

In some embodiments of the method, the subject is in need of local anesthesia or analgesia in nerve tissue including injured sensory neurons.

In some embodiments of the method, the compound is administered by injection or topically. In some embodiments of the method, the topical administration is ophthalmic topical administration.

The presently-disclosed subject matter is further inclusive of pharmaceutical compositions including a compound selected from those set forth in Table A, or a pharmaceutically-acceptable salt thereof.

In some embodiments, the composition is provided for producing local anesthesia or analgesia in nerve tissue of a subject and/or for treating neuropathic pain in a subject, and includes the compound, or pharmaceutically-acceptable salt thereof, and a second local anesthetic. In some embodiments, the second local anesthetic is an amino ester. In some embodiments, the second local anesthetic is an amino amide.

In some embodiments the composition also includes an adjuvant, which is not an alpha-2 adjuvant. In some embodiments the compound includes an adjuvant, which is not an alpha-2 adjuvant and the compound is:

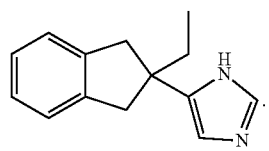 [SMILES: CCC1(c2cnc[nH]2)Cc2ccccc2C1]

In some embodiments, the adjuvant is selected from epinephrine, narcotics, buprenorphine, muscle relaxants, non-steroidal anti-inflammatories (such as Toradol), Hyaluronidase, bicarbonate, and dexamethasone.

In some embodiments of the presently-disclosed subject matter, a pharmaceutical composition is provided, which includes, comprising a compound, or a pharmaceutically-acceptable salt thereof, selected from those set forth in Table A, and pharmaceutically acceptable carrier.

In some embodiments, the pharmaceutically-acceptable carrier is for topical ophthalmic administration. In some embodiments, the composition is formulated in an eye drop, an eye wash, or an eye ointment.

In some embodiments, the composition is prepared for local administration to provide a local or regional anesthesia or analgesia in nerve tissue effect, and not a systemic effect. The composition can be prepared for topical delivery. In some embodiments, the composition is formulated in a spray.

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
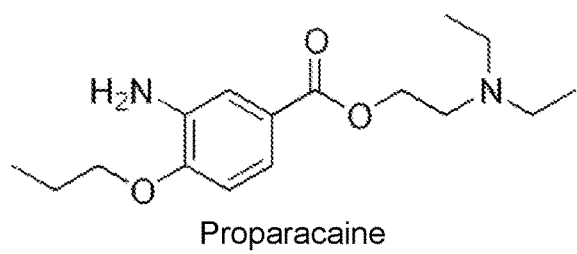
FIG. 1 includes the structure of known local anesthetics, as well as an example of a compound for use in accordance with the present-disclosed subject matter.
Figure 1:
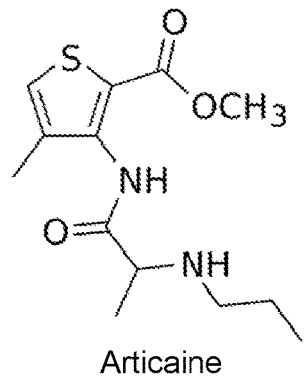
Figure 1:
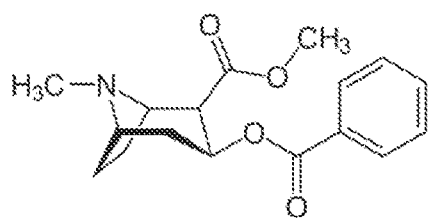
Figure 1:
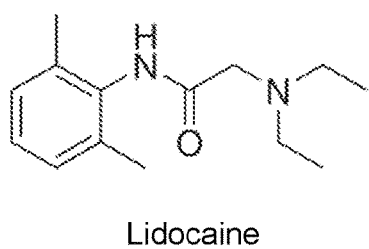
Figure 1:
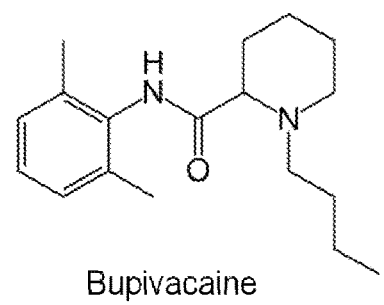
Figure 1:
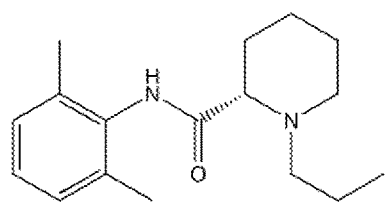
Figure 1:
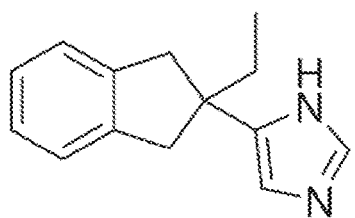

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes pharmaceutical compositions and methods for producing local or regional anesthesia and analgesia in a nerve or nerve tissue of a subject. As will be known by those of ordinary skill in the art, nerve tissue is comprised on neurons or nerve cells, which include a cell body (soma), dendrites, and an axon or nerve fiber. Types of neurons include sensory neurons, which respond to touch, sound, light, and other stimuli, and motor neurons that receive signals from the brain and spinal cord to cause muscle contractions and affect glandular outputs.

These compositions and methods make use of compounds that are structurally-dissimilar from the 'caine-family of local anesthetics and represent a unique set of anesthetic agents. These compounds include those set forth in Table A.

TABLE A

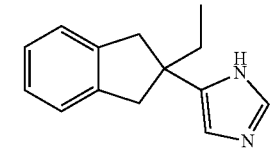 [SMILES: CCC1(c2cnc[nH]2)Cc2ccccc2C1]

4(5)-(2,3-dihydro-2-ethyl-1H-inden-2-yl)imidazole

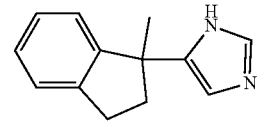

5-(2,3-dihydro-1-methyl-1H-inden-1-yl)-1H-imidazole

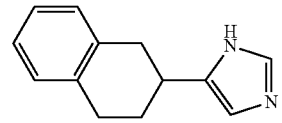 [SMILES: c1ccc2c(c1)CCC(c1cnc[nH]1)C2]

5-(1,2,3,4-tetrahydronaphthalen-2-yl)-1H-imidazole

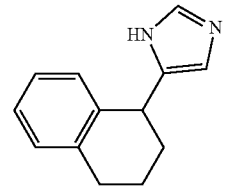 [SMILES: c1ccc2c(c1)CCCC2c1cnc[nH]1]

5-(1,2,3,4-tetrahydronaphthalen-1-yl)-1H-imidazole

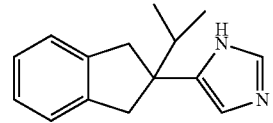 [SMILES: CC(C)C1(c2cnc[nH]2)Cc2ccccc2C1]

5-(2-isopropyl-2,3-dihydro-1H-inden-2-yl)-

TABLE A-continued 1H-imidazole

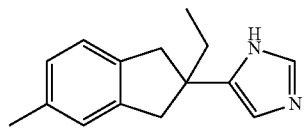 [SMILES: CCC1(c2cnc[nH]2)Cc2ccc(C)cc2C1]

5-(2-ethyl-5-methyl-2,3-dihydro-1H-inden-2-yl)-1H-imidazole

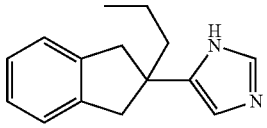 [SMILES: CCCC1(c2cnc[nH]2)Cc2ccccc2C1]

5-(2-propyl-2,3-dihydro-1H-inden-2-yl)-1H-imidazole

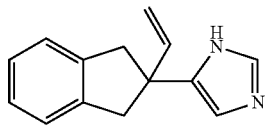 [SMILES: C=CC1(c2cnc[nH]2)Cc2ccccc2C1]

5-(2-vinyl-2,3-dihydro-1H-inden-2-yl)-1H-imidazole

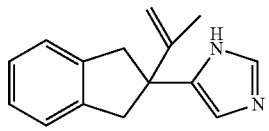 [SMILES: C=C(C)C1(c2cnc[nH]2)Cc2ccccc2C1]

5-(2-(prop-1-en-2-yl)-2,3-dihydro-1H-inden-2-yl)-1H-imidazole

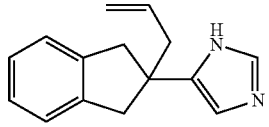 [SMILES: C=CCC1(c2cnc[nH]2)Cc2ccccc2C1]

5-(2-allyl-2,3-dihydro-1H-inden-2-yl)-1H-imidazole

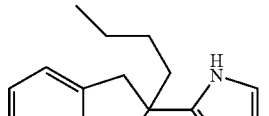

5-(2-butyl-2,3-dihydro-1H-inden-2-yl)-1H-imidazole

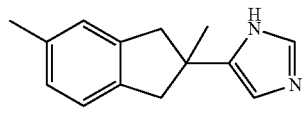

5-(2,5-dimethyl-2,3-dihydro-1H-inden-2-yl)-1H-imidazole

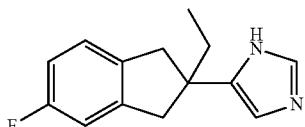

5-(2-ethyl-5-fluoro-2,3-dihydro-1H-inden-2-yl)-1H-imidazole

TABLE A-continued

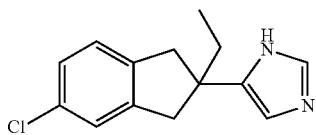 [SMILES: CCC1(c2cnc[nH]2)Cc2ccc(Cl)cc2C1]

5-(5-chloro-2-ethyl-2,3-dihydro-1H-inden-2-yl)-1H-imidazole

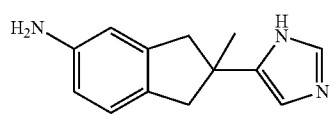

2-(1H-imidazol-5-yl)-2-methyl-2,3-dihydro-1H-inden-5-amine

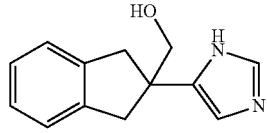 [SMILES: OCC1(c2cnc[nH]2)Cc2ccccc2C1]

(2-(1H-imidazol-5-yl)-2,3-dihydro-1H-inden-2-yl)methanol

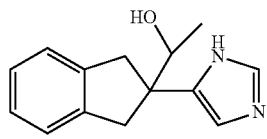

1-(2-(1H-imidazol-5-yl)-2,3-dihydro-1H-inden-2-yl)ethanol

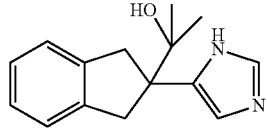 [SMILES: CC(C)(O)C1(c2cnc[nH]2)Cc2ccccc2C1]

2-(2-(1H-imidazol-5-yl)-2,3-dihydro-1H-inden-2-yl)propan-2-ol

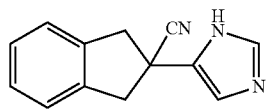

2-(1H-imidazol-5-yl)-2,3-dihydro-1H-indene-2-carbonitrile

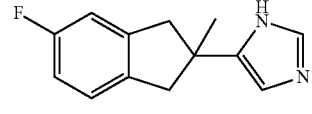 [SMILES: CC1(c2cnc[nH]2)Cc2ccc(F)cc2C1]

5-(5-fluoro-2-methyl-2,3-dihydro-1H-inden-2-yl)-1H-imidazole

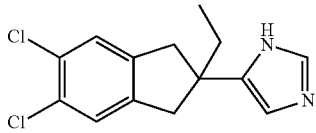 [SMILES: CCC1(c2cnc[nH]2)Cc2cc(Cl)c(Cl)cc2C1]

5-(5,6-dichloro-2-ethyl-2,3-dihydro-1H-inden-2-yl)-1H-imidazole

TABLE A-continued

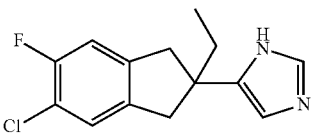 [SMILES: CCC1(c2cnc[nH]2)Cc2cc(F)c(Cl)cc2C1]

5-(5-chloro-2-ethyl-6-fluoro-2,3-dihydro-
1H-inden-2-yl)-1H-imidazole

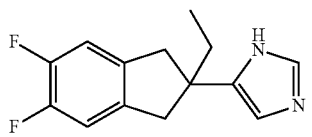 [SMILES: CCC1(c2cnc[nH]2)Cc2cc(F)c(F)cc2C1]

5-(2-ethyl-5,6-difluoro-2,3-dihydro-1H-
inden-2-yl)-1H-imidazole

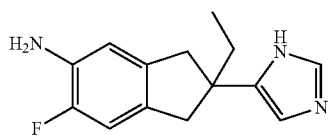 [SMILES: CCC1(c2cnc[nH]2)Cc2cc(N)c(F)cc2C1]

2-ethyl-6-fluoro-2-(1H-imidazol-5-yl)-2,3-
dihydro-1H-inden-5-amine

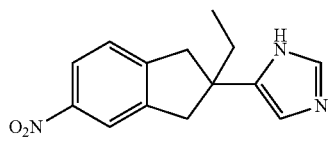 [SMILES: CCC1(c2cnc[nH]2)Cc2ccc([N+](=O)[O-])cc2C1]

5-(2-ethyl-5-nitro-2,3-dihydro-1H-inden-2-
yl)-1H-imidazole

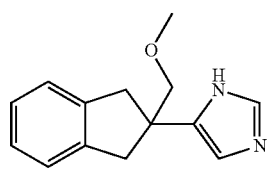 [SMILES: COCC1(c2cnc[nH]2)Cc2ccccc2C1]

5-(2-(methoxymethyl)-2,3-dihydro-1H-
inden-2-yl)-1H-imidazole

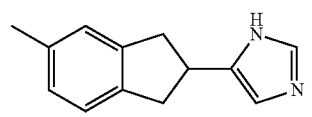

5-(5-methyl-2,3-dihydro-1H-inden-2-yl)-
1H-imidazole

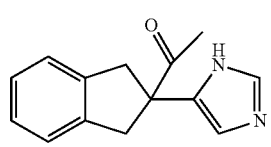 [SMILES: CC(=O)C1(c2cnc[nH]2)Cc2ccccc2C1]

1-(2-(1H-imidazol-5-yl)-2,3-dihydro-1H-
inden-2-yl)ethanone

The first of these compounds identified in Table A, and also depicted in FIG. 1, is known as "atipamezole" or "Atip." Atipamezole is currently indicated for the reversal of the sedation and the systemic analgesic effects induced by administration of medetomidine and dexmedetomidine in animals, particularly dogs.

Atipamezole was designed as an $\alpha_2$ adrenergic receptor antagonist and is available under the brand name ANTISEDAN® from Pfizer, Inc. (New York, N.Y.). The compound has also been suggested for use in treating Parkinson's disease, development of dyskinesias, impotence and sexual dysfunction, age-related cognitive disorders, epilepsy, depression, parasitic infection, and for use in attenuating alcohol intoxication.

As disclosed herein, it was surprisingly discovered that Atipamezole can exert local and/or regional anesthetic action, which has never before been proposed or suggested. The local anesthetic effect of Atip is also independent of its $\alpha_2$AR antagonist function.

Accordingly, in some embodiments of the presently-disclosed subject matter, a method of producing anesthesia in a nerve is provided, involves administering to the nerve an effective amount of a compound as set forth in Table A or a pharmaceutically-acceptable salt thereof. In some embodiments, a method of producing local or regional anesthesia or analgesia in nerve tissue of a subject involves administering an effective amount of Atip or a pharmaceutically-acceptable salt thereof to the subject.

In some embodiments, the method also involves identifying the subject as having a need for local anesthesia or analgesia. In some embodiments, the method can involve identifying the subject as being in need of treatment for a condition selected from the group consisting of neuropathic, inflammatory, post-surgical, trauma-induced, visceral distension-induced (e.g., being in labor in pregnancy, bowel impaction), neurodegenerative (genetic-, drug-, or disease-induced), cancer-induced, and tissue degeneration-induced, pain or dysesthesia. In some embodiments, the method can involve identifying a subject as in need of treatment for ocular traumas (such as physical, chemical and thermal insult), ocular surgeries (such as keratoplasty or LASIK surgery), corneal erosions as a complication of diabetes or a side effect of certain anti-cancer drugs, and dry eye disease. In some embodiments, the method can administering the compound to an open wound. In some embodiments, the subject has a condition selected from conditions such as trauma, burns, pressure sores, and disease states such as epidermolysis bullosa (EB). In some embodiments, the subject is undergoing intraoperative lavage.

In some embodiments, the method can involve identifying a subject in need of treatment in the context of dental, obstetrics, or ambulatory surgery. In some embodiments, the subject can have a rib fracture (e.g., patches including the compound). In some embodiments, the compound can be used as a general anesthetic adjunct.

As used herein, the term "subject" refers to a target of administration and includes both human and animal subjects. Thus, veterinary therapeutic uses are provided in accordance with the presently disclosed subject matter.

As used herein, the terms "treatment" or "treating" relate to any treatment of a condition as disclosed herein or associated with a need for producing local or regional anesthesia or analgesia in nerve tissue of a subject, including but not limited to prophylactic treatment to prevent development or reduce severity of a disorder, as well as therapeutic treatment. In this regard, it is understood that prophylactic treatment does not refer to a complete prevention of any sign of the condition, but rather to a reduction of risk of developing the condition and/or reducing the severity of the condition. In this regard, it is also understood that therapeutic treatment can relate to curing or substantially curing a condition, as well as ameliorating at least one symptom of the condition and/or reducing the severity of the condition and/or symptom.

As used herein, the terms "local anesthesia" and "regional anesthesia" refer to a reversible local numbness and/or analgesia, or the reversible effect produced by the compositions and methods disclosed herein when administered locally (e.g., topically, infiltration, injection, etc.) that provides localized or regionalized full or partial inhibition of sensory perception or pain sensation.

As noted above, it was a surprising discovery that compounds as disclosed herein can exert local and/or regional anesthetic action, which has never before been proposed or suggested. Indeed, the discovery that these compounds can produce local anesthesia is unexpected. With reference to FIG. 1, the compounds are structurally dissimilar to existing local anesthetic agents, which are generally either ester-linked local anesthetics (LAs) (also referred to as amino esters) or amine-linked LAs (also referred to as amino amines). Structurally, these local anesthetics consist of three molecular components: a lipophilic part, an intermediate aliphatic chain, and a hydrophilic (amine) part. The chemical linkage between the lipophilic part and the intermediate chain can be of the amide-type or the ester-type, and is the general basis for the current classification of local anesthetics.

Examples of ester-linked LAs or amino esters include, but are not limited to, Benzocaine, Chloroprocaine, Cocaine, Cyclomethycaine, Dimethocaine (Larocaine), Piperocaine, Propoxycaine, Procaine (Novocaine), Proparacaine, and Tetracaine (Amethocaine). Ester-linked LAs are hydrolyzed at the ester linkage in plasma by pseudocholinesterase. The rate of hydrolysis of ester-linked LAs depends on the type and location of the substitution in the aromatic ring. For example, 2-chloroprocaine is hydrolyzed about four times faster than procaine, which in turn is hydrolyzed about four times faster than tetracaine. However, the rate of hydrolysis of all ester-linked LAs is markedly decreased in patients with atypical plasma pseudocholinesterase, and a prolonged epidural block in a patient with abnormal pseudocholinesterase has been reported. Another hallmark of metabolism of ester-linked LAs is that their hydrolysis leads to the formation of para-aminobenzoic acid (PABA). PABA and its derivatives carry a small risk potential for allergic reactions.

Examples of amine-linked LAs or amino amines include, but are not limited to, Articaine, Bupivacaine, Cinchocaine (Dibucaine), Etidocaine, Levobupivacaine, Lidocaine (Lignocaine), Mepivacaine, Prilocaine, Ropivacaine, and Trimecaine. As opposed to ester-linked drugs, amide-linked LAs are metabolized in the liver by a dealkalization reaction in which an ethyl group is cleaved from the tertiary amine. The hepatic blood flow and liver function determine the hepatic clearance of these anesthetics. Consequently, factors that decrease hepatic blood flow or hepatic drug extraction both result in an increased elimination half-life. Renal clearance of unchanged LAs is a minor route of elimination, accounting for only 3% to 5% of the total drug administered.

As apparent from certain of the described features of ester-linked LAs and amine-linked LAs, they can have certain drawbacks, and can be contraindicated for certain subjects. In some embodiments, the presently-disclosed method can involve identifying the subject as having a resistance or an allergy an amino ester and/or an amino amide local anesthetic.

In some embodiments, the subject is identified as having a resistance or allergy is to an amino ester local anesthetic. In some embodiments, the subject is identified as having liver disease, in which embodiments, it is noted that amino amide LAs are metabolized in the liver and may be contraindicated as an alternative for a subject with liver disease, compounding the issue would be if the subject was also allergic to amino ester LAs.

In some embodiments, the subject is identified as having a resistance or allergy to an amino amide local anesthetic. In some embodiments, the subject is identified as having atypical plasma pseudocholinesterase, in which embodiments, it is noted that amino esters LAs are hydrolyzed by pseudocholinesterase, with the rate of hydrolysis being significantly reduced in subjects with atypical plasma pseudocholinesterase, such that amino ester LAs may be contraindicated as an alternative, compounding the issue would be if the subject was allergic to amino amide LAs.

In some embodiments of the method disclosed herein, it can be desirable to administer a second anesthetic, in addition to a compound from Table A, such as Atip. For example, where there is not an allergy and/or no contraindication, in addition to a compound from Table A, an LA selected from an amino ester and an amino amide can be administered. In some embodiments, the second anesthetic is an amino ester. In some embodiments, the second anesthetic is an amino amide. In some embodiments, in addition to a compound from Table A, both an amino ester and an amino amide are administered. In some embodiments, co-administration of a compound from Table A with one or more additional anesthetics produces an additive or synergistic effect.

Embodiments of the methods disclosed herein can also involve co-administration of an adjunct or adjuvant, which is not an alpha-2-agonist. Alpha-2-agonists, such as clonidine or dexmedetomidine, would not be co-administered in accordance with the present invention, because, for example, Atip is a direct antagonist. In this regard, examples of appropriate adjuncts or adjuvants for use in accordance with the present invention include, but are not limited to, epinephrine, narcotics, buprenorphine, muscle relaxants, non-steroidal anti-inflammatories (such as Toradol), Hyaluronidase, bicarbonate, and dexamethasone. Embodiments of the methods disclosed herein can also involve co-administration of a local anesthetic adjunct. Embodiments of the methods disclosed herein can also involve co-administration of a narcotic, buprenorphine (agonist/antagonist), muscle relaxant, Nosteriodal (toradol), Hyaluronidase, bicarbonate, and/or dexamethasone.

The presently-disclosed invention is inclusive of pharmaceutical compositions for producing local anesthesia or analgesia in nerve tissue of a subject and/or for treating a condition in a subject (e.g., neuropathic, inflammatory, post-surgical, trauma-induced, visceral distension-induced (e.g., being labor in pregnancy, bowel impaction), neurodegenerative (genetic-, drug-, or disease-induced), cancer-induced, and tissue degeneration-induced, pain or dysesthesia), which include a compound from Table A, such as Atip, or a pharmaceutically-acceptable salt thereof, and a second local anesthetic, an adjuvant, and/or other existing agents, as will become apparent to one of ordinary skill in the art upon study of this document.

It was surprisingly discovered that Atip preferentially acts on sensory axons over motor axons, such that when sensory axons are blocked, some motor axons can still conduct electrical signal. As such, in some embodiments, the method involves identifying a subject in need of a level of retained motor function. As will be appreciated by one of ordinary skill in the art, this is a highly desirable feature, and informs utility in a number of applications.

For example, in the context of dental applications, use can result in less facial paralysis and drooling issues after dental work, as compared to existing methods of LA. Thus, in some embodiments, the method involves a subject who is a dental patient. In some embodiments of the method, a compound from Table A can be administered prior to a dental procedure.

For another example, in the context of obstetrical applications, use can result in reduced influence on motor outflow while still providing block of labor pain. Furthermore, use can result in a reduced risk associated with a condition called "high spinal anesthesia" where the existing anesthetics, which block conduction in both sensory and motor neurons, can flow upward to the part of spinal cord with motor control of breathing, causing potentially serious issues with the ability to breathe. In this regard, in some embodiments, the method involves a subject who is an obstetric patient. In some embodiments of the method, a compound from Table A can be administered during labor.

For another example, in the context of ocular applications, use can result in treating pain, while avoiding delay in wound healing and severe risk of corneal degradation. In this regard, in some embodiments, the method involves a subject who has had an ocular trauma, ocular surgery, corneal erosions, or dry eye disease. In some embodiments of the method, a compound from Table A can be administered to a subject having ocular pain.

For yet another example, in certain veterinary applications, post-procedural paralysis/paresis can occur and is very stressful for animals and they often injure themselves at this time; however, with the method disclosed herein, pain control can be provided but at least some motor control would alleviate much of the stress. As noted hereinabove, Atip is currently administered following a veterinary procedure to revive an animal from alpha-2 based sedation. The distinction of the method proposed here is that Atip is administered prior to procedure for LA purposes. The administration can be directly into nervous tissue, such as a nerve. In this regard, it is likely that an alpha-2 based sedation would not be used. As such, the use of a compound from Table A as an LA in this context will prevent and/or alleviate symptoms of post-procedural paralysis/paresis, which is stressful for animals and often causes them to injure themselves. The compound would provide for some LA/pain control, but allow at least some motor control to alleviate the stress. In this regard, in some embodiments of the presently-disclosed subject matter, the subject is an animal and the compound is administered prior to a procedure. In some embodiments, the procedure is one for which the animal will be administered general sedation. In some embodiments, the general sedation is not an alpha-2 based sedation. In some embodiments, the sedation includes use of acepromazine, ketamine, xylazine, a barbiturate, or an anticholinergic.

The presently-disclosed subject matter is inclusive of a pharmaceutical composition that includes a compound, or a pharmaceutically-acceptable salt thereof, selected from the compounds set forth in Table A, and pharmaceutically acceptable carrier.

The presently-disclosed subject matter is inclusive of a pharmaceutical composition that includes a compound, or a pharmaceutically-acceptable salt thereof, selected from the compounds set forth in Table A, and pharmaceutically acceptable carrier. In some embodiments, the pharmaceutically-acceptable carrier is for topical ophthalmic administration.

In some embodiments, the composition is prepared for local administration to provide a local or regional anesthesia or analgesia in nerve tissue effect, and not a systemic effect. In some embodiments, the composition is prepared for topical delivery. In some embodiments, the composition is formulated in a spray. In some embodiments, the composition is formulated in an eye drop, an eye wash, or an eye ointment.

"Pharmaceutically acceptable carriers" are known in the art and can be selected for the form of the composition, desired administration route, and the like. Accordingly, the compositions are formulated in accordance with methods known in the art for the particular route of administration desired. In some embodiments, the compositions are preferably administered topically. In some embodiments, the compositions are preferably administered topically to the eye.

Compositions administered according to the presently-disclosed subject matter comprise a pharmaceutically effective amount of a compound as set forth in Table A. As used herein, a "pharmaceutically effective amount" is one which is sufficient to produce local anesthesia or regional anesthesia. Generally, the compound in the composition will be provided at a concentration of about 10 to about 4000 uM. As will be understood by those of ordinary skill in the art, the appropriate concentration will vary depending on the mode of administration. For example, for topical formulations, the concentration would be higher than for injectable formulations. In some embodiments, the composition will be provided at a concentration of about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 375, 380, 385, 390, 395, 400, 405, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 uM. In some embodiments, the composition will be provided at a concentration of about 1, 2, 3, 4, 5, 6, 7, 8, 9 or 10 mM. In some embodiments, the composition will be provided at a concentration of about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 uM, but not more than about, 305, 310, 315, 320, 325, 330, 335, 340, 345, 350, 355, 360, 375, 380, 385, 390, 395, or 400 uM. In some embodiments, the composition will be provided at a concentration of about 400, 405, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, or 995 uM, but not more than about, 1, 2, 3, 4, 5, 6, 7, 8, 9, or 10 mM.

Compositions administered according to the presently-disclosed subject matter can be formulated as solutions, suspensions and other dosage forms for topical administration. For ocular administration, aqueous solutions are generally desirable, based on ease of formulation, as well as a subject's ability to easily administer such compositions by means of instilling one to two drops of the solutions in the affected eyes. However, the compositions may also be suspensions, viscous or semi-viscous gels, or other types of solid or semi-solid compositions.

The compositions administered according to the presently-disclosed subject matter can also include various other ingredients, including but not limited to surfactants, tonicity agents, buffers, preservatives, co-solvents and viscosity building agents.

Various tonicity agents may be employed to adjust the tonicity of the composition, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably, however, the buffer will be chosen to maintain a target pH within the range of pH 6-7.5.

Compositions formulated for the treatment of ocular administration can also comprise aqueous carriers designed to provide immediate, short-term relief of dry eye-type conditions. Such carriers can be formulated as a phospholipid carrier or an artificial tears carrier, or mixtures of both. As used herein, "phospholipid carrier" and "artificial tears carrier" refer to aqueous compositions which: (i) comprise one or more phospholipids (in the case of phospholipid carriers) or other compounds, which lubricate, "wet," approximate the consistency of endogenous tears, aid in natural tear build-up, or otherwise provide temporary relief of dry eye symptoms and conditions upon ocular administration; (ii) are safe; and (iii) provide an appropriate delivery vehicle for the topical administration of an inhibitor of acyl-CoA synthetase. Examples of artificial tears compositions useful as artificial tears carriers include, but are not limited to, commercial products, such as Tears Naturale®, Tears NaturaleII®, Tears Naturale Free®, and Bion Tears® (Alcon Laboratories, Inc., Fort Worth, Texas). Examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention.

Other compounds designed to lubricate, "wet," approximate the consistency of endogenous tears, aid in natural tear build-up, or otherwise provide temporary relief of dry eye symptoms and conditions upon ocular administration of the eye are known in the art. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P.

Other compounds can also be added to the ophthalmic compositions to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoise ("cps").

Topical ophthalmic products can be packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

As will be recognized by one of ordinary skill in the art, there are a number of other settings in which producing local or regional anesthesia or analgesia in nerve tissue while retaining motor control is highly desirable, for example, in connection with military field anesthesia, obstetrics, dentistry, and as a treatment for pain.

It was surprisingly discovered that Atip blocks the action potentials of both normal and injured sensory neurons. In this regard, in some embodiments, the subject is in need of local anesthesia or analgesia in nerve tissue including injured sensory neurons. Examples or relevant conditions associated with injured sensory neurons include, but are not limited to, skin incision or abrasion, nerve injury due to trauma, surgery, or neurodegeneration, inflammation, and tissue degeneration or damage (e.g., arthritis, bone fracture, etc.).

In accordance with the presently-disclosed subject matter, administration can occur in a number of manners, with examples including, but not limited to: injection (e.g., perinerve, epidural, tissue infiltration including dental, etc.; in some embodiments, IM or IV), topical, ophthalmic (e.g., eye wash or eye drops), and spray (e.g., intra-nasal, throat, cutaneous for abrasions, etc.). In some embodiments, administration can occur via a device that is coated with a compound as set forth in Table A or a pharmaceutical composition thereof, for example, an endogastric or endotracheal tubes prior to insertion.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

A surgical preparation was used to determine whether Atip acts differently on sensory or motor neurons. The procedures used were similar to those described in Petruska et al., 1998 (Experimental Brain Research 121:379-390). Briefly, adult rats received general anesthesia with ketamine/xylazine. The jugular vein, carotid artery, and trachea were intubated for the purposes of administering supplementary anesthesia, monitoring of blood pressure, and measuring end-expired $CO_2$, respectively. Normal body temperature was maintained within 1° C. via a water-based thermal blanket. A laminectomy (T13 to L2) was performed to expose the L4-L6 dorsal roots and ventral roots, which were sectioned from the spinal cord.

Figure 2A:
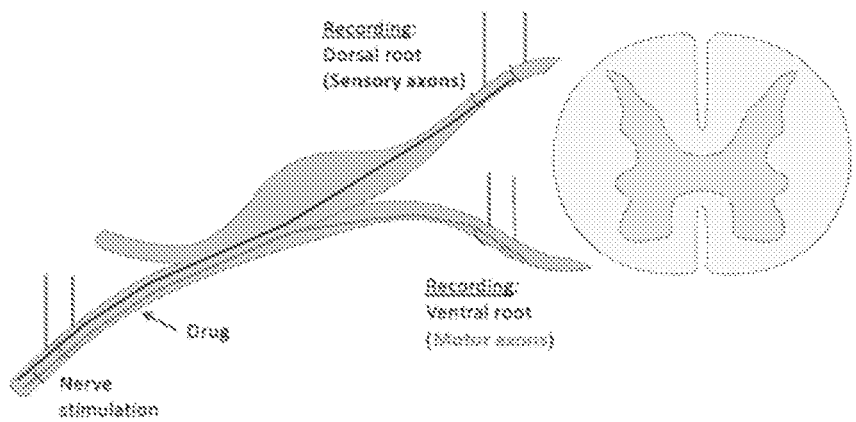
FIG. 2A is a schematic of a surgical preparation to examine whether a compound, applied directly to the nerve, can block conduction of signals evoked by electrical stimulation of the nerve and carried by sensory axons (Dorsal Root) or motor axons (Ventral Root).

Separate and simultaneous recording of activity in sensory and motor axons was achieved using separate sets of bipolar electrodes. The left-side branches of the sciatic nerve (the caudal cutaneous sural (CCS), tibial, and peroneal nerves) were exposed the popliteal fossa near the ankle for placement of the distal bipolar electrodes which delivered square-wave stimulation in the A-beta, A-delta, and C-fiber ranges. A 10-12 mm segment of the left lumbar plexus was exposed lateral to the sacrum. This exposure was separate from that use for the sciatic nerve branches, with enough tissue between to prevent any exchange of fluids between the exposures. Drugs were applied to the lumbar plexus exposure. FIG. 2A is a schematic of the surgical preparation, Blue hooks represent bipolar electrodes.

Compound action potentials (CAPs) were generated by stimulating the sciatic nerve branches. The CAPs propagated centrally through the lumbar plexus to the dorsal and ventral roots where the sensory and motor CAPs (sCAP and mCAP) were detected with the recording electrodes. Effectiveness of conduction block was assessed by measuring the properties of the CAPs (peak and area) conducted through the lumbar plexus exposure and treated with drug compared to the CAPs in the control condition (vehicle or saline in the lumbar plexus exposure).

Figure 2B:
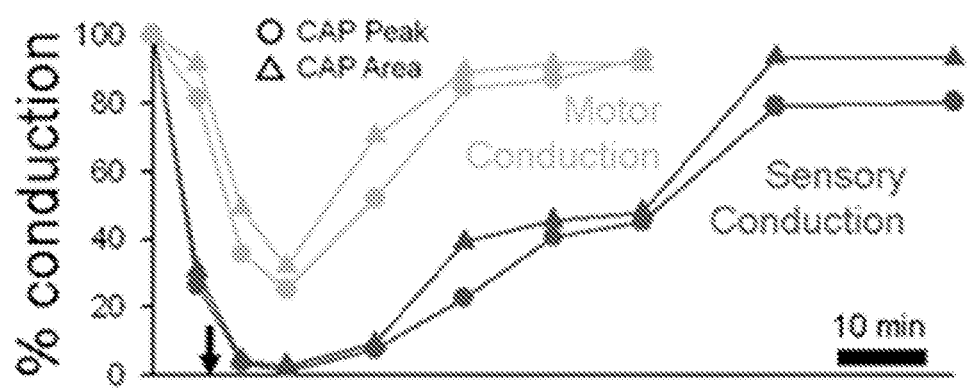
FIG. 2B includes the results of a study using the preparation of FIG. 2A, and assesses the effectiveness of conduction block by measuring properties of the compound action potentials (CAPs) (peak and area) conducted through the lumbar plexus exposure.

With reference to FIG. 2B, activity in response to electrical stimulation of the peroneal nerve was recorded from sensory and motor fascicles (20-30 sweeps averaged per time point). 100 ul of Atip undiluted clinical dose [5 mg/ml] was applied topically to a small pool created over the sciatic nerve. The arrow on the y-axis indicates Atip wash-out. CAP peak amplitude and area for each time were normalized to baseline (pre-application). CAP area is measured as a control because conduction delay could affect CAP peak similarly to actual conduction block. Measuring both together avoids false-positives. Such a similar course for peak amplitude and area strongly indicates conduction block, not conduction delay.

As illustrated by these data, the compound can act rapidly, is reversible (it does not permanently-block conduction), and is effective longer (preferentially) on sensory neurons than on motor neurons. Also, the measurements (CAP peak and area) indicate that the action is a blocking of conduction, not simply slowing down conduction so much that the detection system cannot see it (block vs. delay).

The recordings in FIGS. 2A and 2B focus on the large-diameter fibers, but do not address whether Atip blocks conduction in the small-diameter fibers responsible for the majority of peripheral pain-signals. To address this, a different model system was used the cutaneous trunk muscle reflex (CTMR), which was previously developed and validated for use in anesthesiology and pain experimentation (4,5).

Figure 3A:
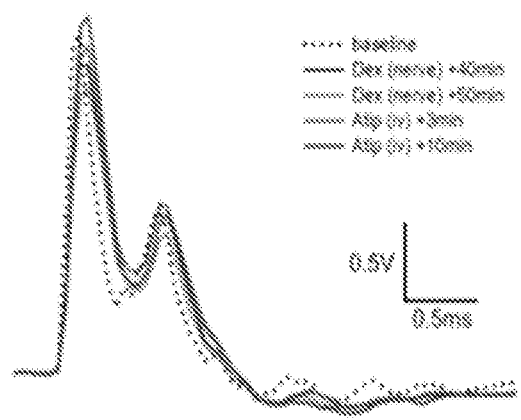
FIG. 3A illustrates the effect of administration of the compound on sensory CAP recordings.

With reference to FIG. 3A, sensory CAP recordings reveal that IV-administered Atip reverses the small conduction block induced by Dex, but does not itself block conduction. These data demonstrates Atip, when used at doses indicated for use as an α-2 AR antagonist, does not act as a local anesthetic.

Figure 3B:
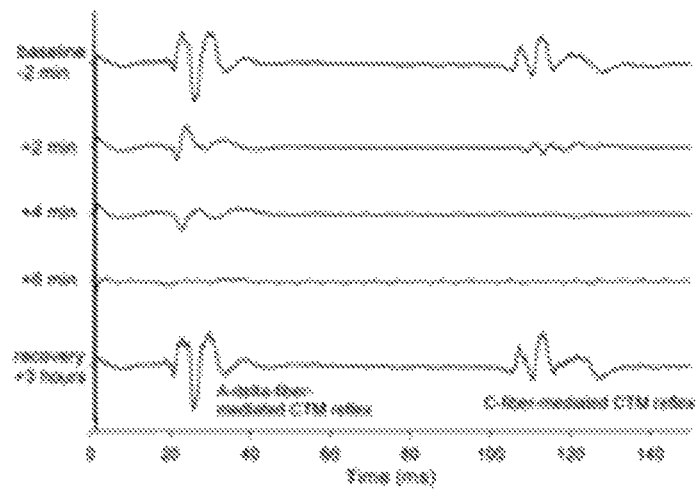
FIG. 3B illustrates the effect of the compound on nociceptor sensory conduction using nociceptive cutaneous trunk muscle (CTM) reflex.

With reference to FIG. 3B, the effects of Atip on nociceptor sensory conduction are assessed using nociceptive CTM reflex as readout. EMG of CTMR induced by electrical stimulation of a sensory nerve treated with Atip (20 ul, 200 uM) reveal that Atip blocks activity in small sensory axons and also does not poison the nerve (EMG returns).

The CTMR in rats appears as a puckering or flicking of the back skin and is elicited only by noxious natural stimulation or by electrical stimulation of sufficient strength to recruit A-delta and C-fibers (4,6,7). Activation of only very few of these sensory axons is sufficient to elicit a CTMR, making the system a "natural amplifier" for small-diameter afferent input and resulting in reflex output detectible at the EMG and behavioral level (4,8).

As illustrated by these data, the drug affected small pain-sensing neurons just as it affected large neurons. It also demonstrates that the neurons are not killed by the drug even when it is not washed out—the conduction returns after a couple hours. FIGS. 2A-3B together support that Atip strongly blocks conduction in both large and small sensory axons, but with relative sparing of conduction in motor axons.

Example 2

Live cell calcium imaging studies were conducted on isolated human DRG Neurons from post mortem donors. Cells were loaded with 3 uM Fluo 8-AM (AAT Bioquest 21081) containing 0.1% Pluronic F-127 (Sigma P2443) for 20 min. The extracellular solution contained in mM (Sigma): 145 NaCl (S3014), 3 KCl (P3911), 2 $CaCl_2$ (C3881), 1 $MgCl_2$ (M9272), 10 HEPES (H3375), 10 glucose (G5767) adjusted to pH 7.4 with NaOH (72068). Fluo-8-loaded cells were excited at 480 nm and emission was collected at 520 nm with a pcoEDGE sCMOS camera (PCO) mounted on an inverted microscope (Olympus IX71).

For Electric Field stimulation (EFs), images were acquired at 100 Hz for 2.5 sec applying simultaneously a train of 10 pulses (5 Hz, 10 ms). After the recording of the baseline profile at Low (1.5 to 2.0 V) and High (2.5 to 3.0 V) Voltage, a pre incubation of 5 mM of the inhibitor is applied to the well before repeating the EFs procedure (Atip 100 uM, Atip 300 uM, Lidocaine 200 uM (Sigma L7757)). The cells that had less than 50% of the pulse response vs the baseline condition was considered inhibited. A washout of 10 min by perfusion was performed after the last EFs procedure.

Lidocaine was first prepared in stock solution using Ethanol (Sigma 459844), Atip was prepared in stock solution using DMSO (Sigma D8418). Image acquisition and data analysis were performed using MetaMorph software (Molecular Devices).

Figure 4:
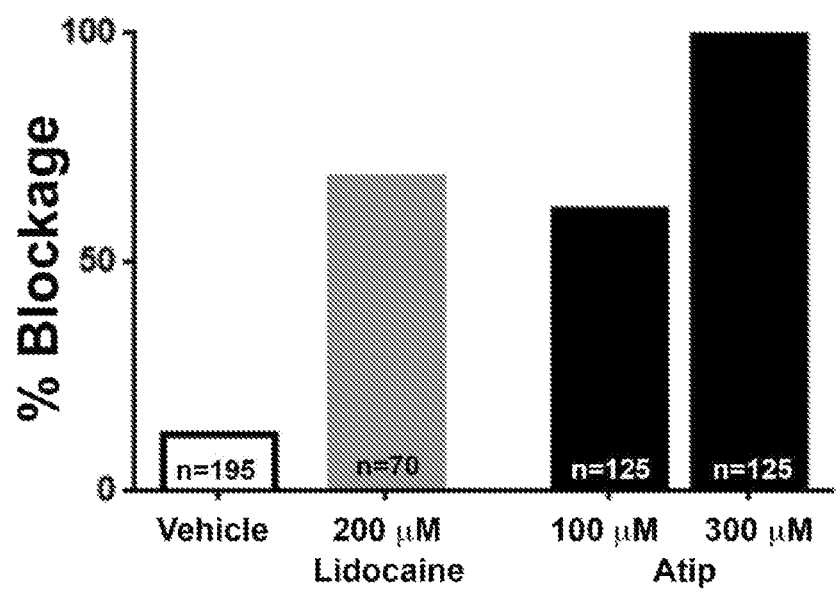
FIG. 4 compares the effect of the compound and lidocaine on the activity of sensory neurons from human donors.

With reference to FIG. 4, optical recordings of action potentials were obtained and revealed that Atip is an effective local anesthetic for human neurons as well. Neurons with less than 50% of the baseline response to electrical field stimulation were considered inhibited. 300 uM Atip blocked activity in 100% of the cells; 100 uM Atip achieved a 62% blockade.

These data illustrate that the effect of Atip is comparable to lidocaine. A therapeutic concentration of lidocaine (200 uM), was less efficacious than the highest tested concentration of Atip, and similar to the lowest concentration of Atip tested.

Example 3

Cytotoxicity studies were performed using Human telomerase-immortalized human corneal epithelial cells (hT-CEpi cells—obtained through Genon Corp., Menlo Park, CA, USA). The cells were plated at a density of 30,000 cells per well of a 96-well dish in growth media (Defined Keratinocyte Media with growth supplement, Invitrogen, Grand Island, NY, USA). After 24 hours of recovery, cells were treated with either growth media alone or growth media supplemented with 0.5% DMSO (vehicle), the indicated concentration of ATIP, or 0.5% proparacaine (Akorn, Forest Lake, IL). Cells were incubated for 24 or 48 hours at 37° C. in 5% $CO_2$. Cell viability was assessed using an Alamar Blue Assay (Thermo Fisher, Waltham, MA, USA).

Figure 5A:
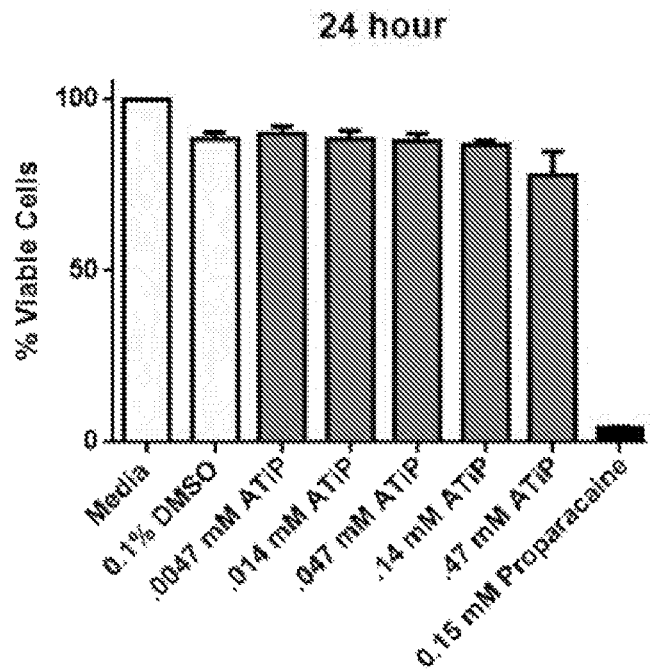
FIG. 5A includes the results of a cytotoxicity profile comparing the compound and propracaine assessed at 24 hours.
Figure 5B:
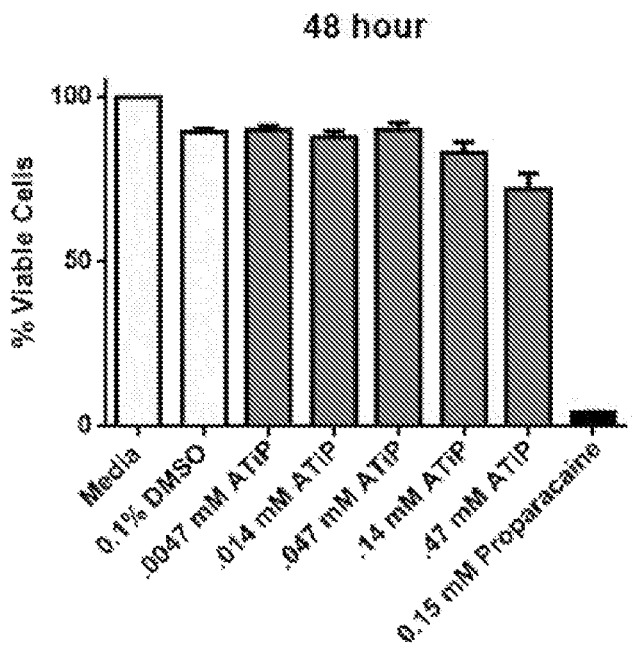
FIG. 5B includes the results of a cytotoxicity profile comparing the compound and propracaine assessed at 48 hours.

With reference to FIGS. 5A and 5B, data are plotted as the fraction of viable cells compared to growth media alone+/− S.E.M (n=3). These data demonstrate that Atip has reduced toxicity, and is thus safer, as compared to the current clinical standard of care (prop arac aine).

Example 4

Studies were conducted to examine the effect of Atip administration on action potentials induced by depolarizing current. Electrophysiology in injury-sensitized dissociated rat sensory neurons was recorded with patch-clamp, using methods previously described (5).

Figure 6:
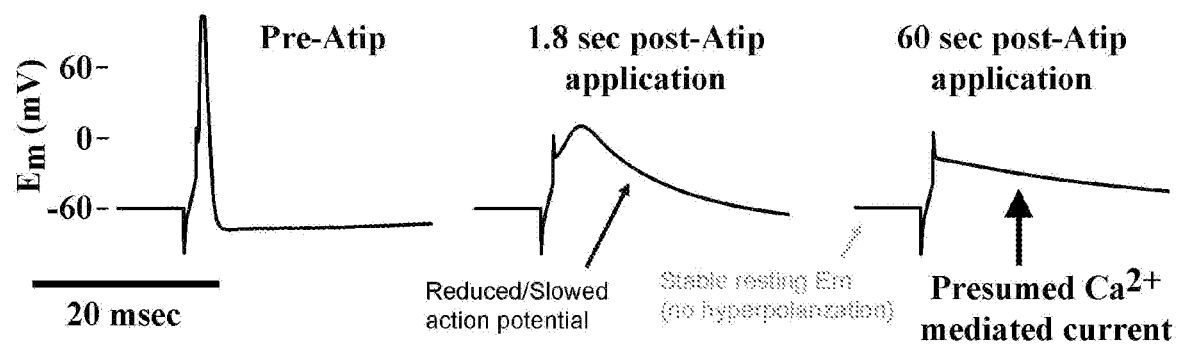
FIG. 6 illustrates the effect of administration of the compound on action potentials induced by depolarizing current.

With reference to FIG. 6, Action potentials induced by depolarizing current (left trace) were rapidly blocked (middle- and right-traces), but some depolarization-activated response still remains (right-trace), suggesting Atip does not block all voltage-activated currents. Atip does not alter the resting membrane potential.

These data demonstrate that Atip rapidly blocks generation of action potentials even in pathologic neurons, and does not induce hyperpolarization. Atip blocks conduction in both large and small axons, but only the small axons have $Ca^{2+}$ currents with their action potentials. This supports that Atip blocks conduction by blocking $Na^+$ channels.

Example 5

Studies testing the effect of Atip were also conducted in α2 receptor subunit knock-out mice. $\alpha_{2A}AR$ knockout and $\alpha_{2C}AR$ knock out mice were used in the study. Animals were injected with 5 mM Atip subcutaneously in their right plantar paw, and vehicle into the left plantar paw. They then received strong pinch to the paw skin and pads on each foot. Right and left paw withdrawal in response to the pinch was assessed.

In each of the wild type, as well as the $\alpha_{2A}AR$ knockout and $\alpha_{2C}AR$ knock out mice, there was withdrawal of the left paw (that received only vehicle) and no withdrawal of the right paw (that received Atip). These data support that Atip does not require α2 receptors for the conduction-blocking effects.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. The Gallup Organization, I. (2008) The 20008 Gallup Study of Dry Eye Sufferers. Princeton, NJ
2. Rush, J. S., Boeving, M. A., Berry, W. L., and Ceresa, B. P. (2014). Antagonizing c-Cbl enhances EGFR-dependent conical epithelial homeostasis. Invest Ophthalmol Vis Sci 55, 4691-4699
3. Boljka, M., Kolar, G., and Vidensek, J. (1994). Toxic side effects of local anaesthetics on the human cornea. Br J Ophthalmol 78, 386-389
4. Petruska, J. C., Barker, D. F., Garraway, S. M., Trainer, R., Fransen, J. W., Seidman, P. A., Soto, R. G., Mendell, L. M., and Johnson, R. D. (2014). Organization of sensory input to the nociceptive-specific cutaneous trunk muscle reflex in rat, an effective experimental system for examining nociception and plasticity. J Comp Neurol 522, 1048-1071
5. Rau, K. K., Hill, C. E., Harrison, B. J., Venkat, G., Koenig, H. M., Cook, S. B., Rabchevsky, A. G., Taylor, B. K., Hai, T., and Petruska, J. C. (2016). Cutaneous tissue damage induces long-lasting nociceptive sensitization and regulation of cellular stress- and nerve injury-associated genes in sensory neurons. Exp Neurol 283, 413-427
6. Theriault, E., and Diamond, J. (1988). Intrinsic organization of the rat cutaneus trunci motor nucleus. J Neurophysiol 60, 463-477
7. Theriault, E., and Diamond, J. (1988). Nociceptive cutaneous stimuli evoke localized contractions in a skeletal muscle. J Neurophysiol 60, 446-462
8. Petruska, J. C., Barker, D. F., Garraway, S. M., Trainer, R., Fransen, J. W., Seidman, P. A., Soto, R. G., Mendell, L. M., and Johnson, R. D. (2013). Organization of sensory input to the nociceptive-specific cutaneous trunk muscle reflex in rat, an effective experimental system for examining nociception and plasticity. The Journal of comparative neurology
9. Huang, Y., Gil, D. W., Vanscheeuwijck, P., Stamer, W. D., and Regan, J. W. (1995). Localization of alpha 2-adrenergic receptor subtypes in the anterior segment of the human eye with selective antibodies. Invest Ophthalmol Vis Sci 36, 2729-2739
10. Woldemussie, E., Wijono, M., and Pow, D. (2007). Localization of alpha 2 receptors in ocular tissues. Vis Neurosci 24, 745-756
11. Robin, A. L. (1997). The role of alpha-agonists in glaucoma therapy. Curr Opin Ophthalmol 8, 42-49
12. Takagi, Y., Osaki, H., Yamashita, T., and Kai, Y. (2016). Prospective Observational Post-marketing Study of Tafluprost 0.0015%/Timolol 0.5% Combination Ophthalmic Solution for Glaucoma and Ocular Hypertension: Short-Term Efficacy and Safety. Ophthalmol Ther
13. Berlan, M., Verhaeghe, S., Pavy-Le Traon, A., Thalamas, C., Lafontan, M., Marques, M. A., Senard, J. M., Parent, M., and Galitzky, J. (2002). Yohimbine administration prevents over-responsiveness to epinephrine induced by simulated microgravity. Aviat Space Environ Med 73, 735-742
14. Christoph, T., Schroder, W., Tallarida, R. J., De Vry, J., and Tzschentke, T. M. (2013). Spinal-supraspinal and intrinsic mu-opioid receptor agonist-norepinephrine reuptake inhibitor (MOR-NRI) synergy of tapentadol in diabetic heat hyperalgesia in mice. J Pharmacol Exp Ther 347, 794-801
15. de Tejada, I. S., Garvey, D. S., Schroeder, J. D., Shelekhin, T., Letts, L. G., Fernandez, A., Cuevas, B., Gabancho, S., Martinez, V., Angulo, J., Trocha, M., Marek, P., Cuevas, P., and Tam, S. W. (1999). Design and evaluation of nitrosylated alpha-adrenergic receptor antagonists as potential agents for the treatment of impotence. J Pharmacol Exp Ther 290, 121-128
16. Karhuvaara, S., Kallio, A., Scheinin, M., Anttila, M., Salonen, J. S., and Scheinin, H. (1990). Pharmacological effects and pharmacokinetics of atipamezole, a novel alpha 2-adrenoceptor antagonist—a randomized, double-blind cross-over study in healthy male volunteers. Br J Clin Pharmacol 30, 97-106
17. Huupponen, R., Karhuvaara, S., Anttila, M., Vuorilehto, L., and Scheinin, H. (1995). Buccal delivery of an alpha 2-adrenergic receptor antagonist, atipamezole, in humans. Clin Pharmacol Ther 58, 506-511
18. Friedenwald, J. S., and Buschke, W. (1944). Some Factors Concerned in the Mitotic and Wound-Healing Activities of the Corneal Epithelium. Trans Am Ophthalmol Soc 42, 371-383
19. Wang, S. B., Hu, K. M., Seamon, K. J., Mani, V., Chen, Y., and Gronert, K. (2012). Estrogen negatively regulates epithelial wound healing and protective lipid mediator circuits in the cornea. FASEB J 26, 1506-1516
20. Meng, I. D., Barton, S. T., Mecum, N. E., and Kurose, M. (2015). Corneal sensitivity following lacrimal gland excision in the rat. Invest Ophthalmol Vis Sci 56, 3347-3354
21. Scott, P. A. (2016) Scott's Anatomy of the Eye and Orbit. Ridgevue Publishing LLC, Boulder, CO
22. Judge, A. J., Najafi, K., Lee, D. A., and Miller, K. M. (1997). Corneal endothelial toxicity of topical anesthesia. Ophthalmology 104, 1373-1379
23. Kadonosono, K., Ito, N., Yazama, F., Nishide, T., Sugita, M., Sawada, H., and Ohno, S. (1998). Effect of intracameral anesthesia on the conical endothelium. J Cataract Refract Surg 24, 1377-1381
24. Kim, W. J., Shah, S., and Wilson, S. E. (1998). Differences in keratocyte apoptosis following transepithelial and laser-scrape photorefractive keratectomy in rabbits. J Refract Surg 14, 526-533
25. Stepp, M. A., Spurr-Michaud, S., and Gipson, I. K. (1993). Integrins in the wounded and unwounded stratified squamous epithelium of the cornea. Invest Ophthalmol Vis Sci 34, 1829-1844
26. Peterson, J. L., Phelps, E. D., Doll, M. A., Schaal, S., and Ceresa, B. P. (2014). The role of endogenous epidermal growth factor receptor ligands in mediating corneal epithelial homeostasis. Invest Ophthalmol Vis Sci 55, 2870-2880
27. Rau, K. K., Petruska, J. C., Cooper, B. Y., and Johnson, R. D. (2014). Distinct subclassification of DRG neurons innervating the distal colon and glans penis/distal urethra based on the electrophysiological current signature. J Neurophysiol 112, 1392-1408
28. Petruska, J. C., Napaporn, J., Johnson, R. D., and Cooper, B. Y. (2002). Chemical responsiveness and histochemical phenotype of electrophysiologically classified cells of the adult rat dorsal root ganglion. Neuroscience 115, 15-30
29. McAlvin, J. B., Zhan, C., Dohlman, J C, Kolovou, P. E., Salvador-Culla, B., and Kohane, D. S. (2015). Corneal Anesthesia With Site 1 Sodium Channel Blockers and Dexmedetomidine. Invest Ophthalmol Vis Sci 56, 3820-3826
30. Sjoholm, B., Landesmaki, J., Pyykko, K., Hillila, M., and Scheinin, M. (1999). Nonadrenergic binding of [3H]atipamezole in rat kidney—regional distribution and comparison to alpha2-adrenoceptors. Br J Pharmacol 128, 1215-1222
31. Rahman, W., D'Mello, R., and Dickenson, A. H. (2008). Peripheral nerve injury-induced changes in spinal alpha (2)-adrenoceptor-mediated modulation of mechanically evoked dorsal horn neuronal responses. J Pain 9, 350-359
32. Wei, H., and Pertovaara, A. (2006). Spinal and pontine alpha2-adrenoceptors have opposite effects on pain-related behavior in the neuropathic rat. Eur J Pharmacol 551, 41-49
33. Sjoholm, B., Savola, J. M., and Scheinin, M. (1995). Nonadrenergic binding of [3H]atipamezole in rat lung. A novel imidazole binding site? Ann N Y Acad Sci 763, 66-77

34. Sjoholm, B., Voutilainen, R., Luomala, K., Savola, J. M., and Scheinin, M. (1992). Characterization of [3H]atipamezole as a radioligand for alpha 2-adrenoceptors. Eur J Pharmacol 215, 109-117
35. Koerber, H. R., Druzinsky, R. E., and Mendell, L. M. (1988). Properties of somata of spinal dorsal root ganglion cells differ according to peripheral receptor innervated. J Neurophysiol 60, 1584-1596
36. Lopez de Armentia, M., Cabanes, C., and Belmonte, C. (2000). Electrophysiological properties of identified trigeminal ganglion neurons innervating the cornea of the mouse. Neuroscience 101, 1109-1115
37. Huang, J., Yang, Y., Dib-Hajj, S. D., van Es, M., Zhao, P., Salomon, J., Drenth, J. P., and Waxman, S. G. (2014). Depolarized inactivation overcomes impaired activation to produce DRG neuron hyperexcitability in a Nav1.7 mutation in a patient with distal limb pain. J Neurosci 34, 12328-12340
38. Park, J., Werley, C. A., Venkatachalam, V., Kralj, J. M., Dib-Hajj, S. D., Waxman, S. G., and Cohen, A. E. (2013). Screening fluorescent voltage indicators with spontaneously spiking HEK cells. PLoS One 8, e85221
39. Jahnsen, J. A., and Uhlen, S. (2013). The C-terminal half of the alpha2C-adrenoceptor determines the receptor's membrane expression level and drug selectivity. Naunyn Schmiedebergs Arch Pharmacol 386, 1031-1040
40. Rush, A. M., Cummins, T. R., and Waxman, S. G. (2007). Multiple sodium channels and their roles in electrogenesis within dorsal root ganglion neurons. J Physiol 579, 1-14
41. Habib, A. M., Wood, J. N., and Cox, J. J. (2015). Sodium channels and pain. Handb Exp Pharmacol 227, 39-56
42. Fan, S. F., Shen, K. F., Scheideler, M. A., and Crain, S. M. (1992). F11 neuroblastoma x DRG neuron hybrid cells express inhibitory mu- and delta-opioid receptors which increase voltage-dependent K+ currents upon activation. Brain Res 590, 329-333
43. Wieringa, P., Tonazzini, I., Micera, S., and Cecchini, M. (2012). Nanotopography induced contact guidance of the F1 1 cell line during neuronal differentiation: a neuronal model cell line for tissue scaffold development. Nanotechnology 23, 275102
44. Ceresa, B. P., and Limbird, L. E. (1994). Mutation of an aspartate residue highly conserved among G-protein coupled receptors results in nonreciprocal disruption of alpha2a-adrenergic receptor-G-protein interactions. J Biol Chem 272, 12121-12124
45. Grant, R. L., and Acosta, D. (1994). Comparative toxicity of tetracaine, proparacaine and cocaine evaluated with primary cultures of rabbit corneal epithelial cells. Exp Eye Res 58, 469-478
46. Farley, D. B., Ford, S. P., Reynolds, L. P., Bhatnagar, R. K., and Van Orden, D. E. (1984). Quantitation of alpha 1-adrenergic receptors in porcine uterine and mesenteric arteries. Am J Obstet Gynecol 150, 485-491
47. Kosugi, T., et al., (2010) High concentrations of dexmedetomidine inhibit compound action potentials in frog sciatic nerves without α2 adrenoceptor activation, British Journal of Pharmacology.
48. Maruta, et al., (2011) Dexmedetomidine and clonidine inhibit the function of Nav1.7 independent of α2-adrenoceptor in adrenal chromaffin cells, J. Anesth 25:549-557.
49. Leem, et al., (2000) Conduction Block by Clonidine is Not Mediated by α2-Adrenergic Receptors in Rat Sciatic Nerve Fibers, Regional Anesthesia and Pain Medicine 25(6): 620-625.
50. Jackson and Ceresa, (2016) Protein Kinase G facilitates EGFR-mediated cell death in MDA-MB-468 cells, Exp Cell Res. 346(2):224-32.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of producing local or regional anesthesia or analgesia in a human nerve or tissue containing a sensory axon or nerve fiber, comprising administering to the human nerve a composition consisting essentially of a compound, or a pharmaceutically-acceptable salt thereof, in an amount that reduces or blocks electrical signal conduction in small sensory axons along the nerve fiber wherein the electrical signal conduction in the small sensory axons is reduced or blocked in an amount that is sufficient to produce local or regional anesthesia or analgesia in the nerve or tissue containing an axon or nerve fiber, wherein the compound or pharmaceutically-acceptable salt thereof is selected from the group consisting of: 5-(2-ethyl-2,3-dihydro-1H-inden-2-yl)-1H-imidazole, 5-(2-isopropyl-2,3-dihydro-1H-inden-2-yl)-1H-imidazole, 5-(2-ethyl-5-methyl-2,3-dihydro-1H-inden-2-yl)-1H-imidazole, 5-(2-propyl-2,3-dihydro-1H-inden-2-yl)-1H-imidazole, 5-(2-vinyl-2,3-dihydro-1H-inden-2-yl)-1H-imidazole, 5-(2-(prop-1-en-2-yl)-2,3-dihydro-1H-inden-2-yl)-1H-imidazole, 5-(2-allyl-2,3-dihydro-1H-inden-2-yl)-1H-imidazole, 5-(2-butyl-2,3-dihydro-1H-inden-2-yl)-1H-imidazole, 5-(2,5-dimethyl-2,3-dihydro-1H-inden-2-yl)-1H-imidazole, 5-(2-ethyl-5-fluoro-2,3-dihydro-1H-inden-2-yl)-1H-imidazole, 5-(5-chloro-2-ethyl-2,3-dihydro-1H-inden-2-yl)-1H-imidazole, 2-(1H-imidazol-5-yl)-2-methyl-2,3-dihydro-1H-inden-5-amine, (2-(1H-imidazol-5-yl)-2,3-dihydro-1H-inden-2-yl) methanol, 1-(2-(1H-imidazol-5-yl)-2,3-dihydro-1H-inden-2-yl) ethanol, 2-(2-(1H-imidazol-5-yl)-2,3-dihydro-1H-inden-2-yl) propan-2-ol, 2-(1H-imidazol-5-yl)-2,3-dihydro-1H-indene-2-carbonitrile, 5-(5-fluoro-2-methyl-2,3-dihydro-1H-inden-2-yl)-1H-imidazole, 5-(5,6-dichloro-2-ethyl-2,3-dihydro-1H-inden-2-yl)-1H-imidazole, 5-(5-chloro-2-ethyl-6-fluoro-2,3-dihydro-1H-inden-2-yl)-1H-imidazole, 5-(2-ethyl-5,6-difluoro-2,3-dihydro-1H-inden-2-yl)-1H-imidazole, 2-ethyl-6-fluoro-2-(1H-imidazol-5-yl)-2,3-dihydro-1H-inden-5-amine, 5-(2-ethyl-5-nitro-2,3-dihydro-1H-inden-2-yl)-1H-imidazole, 5-(2-(methoxymethyl)-2,3-dihydro-1H-inden-2-yl)-1H-imidazole, 5-(5-methyl-2,3-dihydro-1H-inden-2-yl)-1H-imidazole, 1-(2-(1H-imidazol-5-yl)-2,3-dihydro-1H-inden-2-yl) ethanone, 5-(2,3-dihydro-1-methyl-1H-inden-1-yl)-1H-imidazole, 5-(1,2,3,4-tetrahydronaphthalen-2-yl)-1H-imidazole, and 5-(1,2,3,4-tetrahydronaphthalen-1-yl)-1H-imidazole.

2. The method of claim 1, wherein the nerve or tissue containing an axon or nerve fiber is in a human subject.

3. The method of claim 2, and further comprising identifying the human subject as being in need of treatment for a condition selected from the group consisting of neuropathic, inflammatory, post-surgical, trauma-induced, visceral distension-induced, neurodegenerative, cancer-induced, and tissue degeneration-induced, pain or dysesthesia.

4. The method of claim 2 and further comprising identifying the human subject has having a resistance or an allergy an amino ester and/or an amino amide local anesthetic.

5. The method of claim 2, wherein the human subject is in need of a level of retained motor function.

6. The method of claim 2, wherein the compound is administered prior to a dental procedure or during labor.

7. The method of claim 2, wherein the human subject is in need of treatment associated with ocular trauma, ocular surgery, corneal erosions, or dry eye disease.

8. The method of claim 2, wherein the human subject has a condition selected from the group consisting of: open wound, trauma, burn, pressure sore, and epidermolysis bullosa (EB).

9. The method of claim 2, wherein the human subject is undergoing intraoperative lavage.

10. The method of claim 2, wherein the compound is:

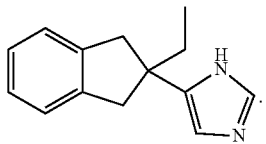 [SMILES: CCC1(c2cnc[nH]2)Cc2ccccc2C1]

11. The method of claim 2, wherein the human subject is in need of local anesthesia or analgesia in tissue containing an axon or nerve fiber injured sensory neurons.

12. The method of claim 2, wherein the compound is administered by injection or topically.

13. The method of claim 12, wherein the topical administration is ophthalmic topical administration.

14. The method of claim 1, wherein the compound or pharmaceutically acceptable salt thereof is administered topically or by injection.

15. The method of claim 14, wherein the compound or pharmaceutically acceptable salt thereof is administered topically to an eye of the subject.

16. The method of claim 1, wherein the method comprises administering the compound to the human nerve in an amount that reduces or blocks electrical signal conduction along C-fibers of the nerve wherein the electrical signal conduction in the C-fibers is reduced or blocked in an amount that is sufficient to produce local or regional anesthesia or analgesia in the nerve or tissue.

17. A method of producing local or regional anesthesia or analgesia in a nerve or tissue containing a sensory axon or nerve fiber in an eye of a human subject, comprising topically administering to an eye of the human subject a composition consisting essentially of 4 (5)-(2,3-dihydro-2-ethyl-1H-inden-2-yl) imidazole:

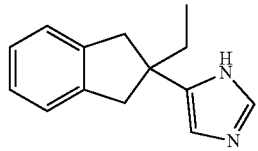 [SMILES: CCC1(c2cnc[nH]2)Cc2ccccc2C1]

4 (5)-(2,3-dihydro-2-ethyl-1H-inden-2-yl) imidazole, or pharmaceutically acceptable salt thereof,
in an amount that reduces or blocks electrical signal conduction in small sensory axons along the nerve fiber in the eye of the human subject wherein the electrical signal conduction in the small sensory axons is reduced or blocked in an amount that is sufficient to produce local or regional anesthesia or analgesia in the nerve or tissue containing an axon or nerve fiber.

18. A method of producing local or regional anesthesia or analgesia in a nerve or tissue containing a sensory axon or nerve fiber in an eye of a human subject, comprising administering to an eye of the human subject a composition consisting of:
a pharmaceutically acceptable carrier; and
a compound, or a pharmaceutically-acceptable salt thereof, in an amount that reduces or blocks electrical signal conduction in small sensory axons along the nerve fiber wherein the electrical signal conduction in the small sensory axons is reduced or blocked in an amount that is sufficient to produce local or regional anesthesia or analgesia in the nerve or tissue containing an axon or nerve fiber,
wherein the compound or pharmaceutically-acceptable salt thereof is selected from the group consisting of: 5-(2-ethyl-2,3-dihydro-1H-inden-2-yl)-1H-imidazole, 5-(2-isopropyl-2,3-dihydro-1H-inden-2-yl)-1H-imidazole, 5-(2-ethyl-5-methyl-2,3-dihydro-1H-inden-2-yl)-1H-imidazole, 5-(2-propyl-2,3-dihydro-1H-inden-2-yl)-1H-imidazole, 5-(2-vinyl-2,3-dihydro-1H-inden-2-yl)-1H-imidazole, 5-(2-(prop-1-en-2-yl)-2,3-dihydro-1H-inden-2-yl)-1H-imidazole, 5-(2-allyl-2,3-dihydro-1H-inden-2-yl)-1H-imidazole, 5-(2-butyl-2,3-dihydro-1H-inden-2-yl)-1H-imidazole, 5-(2,5-dimethyl-2,3-dihydro-1H-inden-2-yl)-1H-imidazole, 5-(2-ethyl-5-fluoro-2,3-dihydro-1H-inden-2-yl)-1H-imidazole, 5-(5-chloro-2-ethyl-2,3-dihydro-1H-inden-2-yl)-1H-imidazole, 2-(1H-imidazol-5-yl)-2-methyl-2,3-dihydro-1H-inden-5-amine, (2-(1H-imidazol-5-yl)-2,3-dihydro-1H-inden-2-yl) methanol, 1-(2-(1H-imidazol-5-yl)-2,3-dihydro-1H-inden-2-yl) ethanol, 2-(2-(1H-imidazol-5-yl)-2,3-dihydro-1H-inden-2-yl) propan-2-ol, 2-(1H-imidazol-5-yl)-2,3-dihydro-1H-indene-2-carbonitrile, 5-(5-fluoro-2-methyl-2,3-dihydro-1H-inden-2-yl)-1H-imidazole, 5-(5,6-dichloro-2-ethyl-2,3-dihydro-1H-inden-2-yl)-1H-imidazole, 5-(5-chloro-2-ethyl-6-fluoro-2,3-dihydro-1H-inden-2-yl)-1H-imidazole, 5-(2-ethyl-5,6-difluoro-2,3-dihydro-1H-inden-2-yl)-1H-imidazole, 2-ethyl-6-fluoro-2-(1H-imidazol-5-yl)-2,3-dihydro-1H-inden-5-amine, 5-(2-ethyl-5-nitro-2,3-dihydro-1H-inden-2-yl)-1H-imidazole, 5-(2-(methoxymethyl)-2,3-dihydro-1H-inden-2-yl)-1H-imidazole, 5-(5-methyl-2,3-dihydro-1H-inden-2-yl)-1H-imidazole, 1-(2-(1H-imidazol-5-yl)-2,3-dihydro-1H-inden-2-yl) ethanone, 5-(2,3-dihydro-1-methyl-1H-inden-1-yl)-1H-imidazole, 5-(1,2,3,4-tetrahydronaphthalen-2-yl)-1H-imidazole, and 5-(1,2,3,4-tetrahydronaphthalen-1-yl)-1H-imidazole.

* * * * *

UNITED STATES PATENT AND TRADEMARK OFFICE
CERTIFICATE OF CORRECTION

PATENT NO. : 12,414,937 B2
APPLICATION NO. : 15/772609
DATED : September 16, 2025
INVENTOR(S) : Jeffrey C. Petruska et al.

It is certified that error appears in the above-identified patent and that said Letters Patent is hereby corrected as shown below:

In the Specification

In Column 2, Line 64, after "amount" insert -- of --.

In Column 2, Line 67, after "is" insert -- : --.

In Column 3, Line 19, after "allergy" insert -- to --.

In Column 3, Line 22, after "allergy" delete "is".

In Column 3, Line 24, after "allergy" delete "is".

In Column 3, Line 35, after "subject" delete "is".

In Column 5, Line 52, delete "propracaine" and insert -- proparacaine --.

In Column 5, Line 55, delete "propracaine" and insert -- proparacaine --.

In Column 11, Line 63, after "allergy" insert -- to --.

In Column 11, Line 66, after "allergy" delete "is".

In Column 12, Line 45, delete "Nosteriodal" and insert -- Nonsteroidal --.

In Column 15, Line 50, delete "Naturalell®," and insert -- Naturale II®, --.

In Column 19, Line 20, delete "CaCl2)" and insert -- (CaCl2) --.

In Column 19, Line 30, delete "mM" and insert -- min --.

Signed and Sealed this
Sixteenth Day of December, 2025

John A. Squires
*Director of the United States Patent and Trademark Office*

CERTIFICATE OF CORRECTION (continued)
U.S. Pat. No. 12,414,937 B2

In Column 20, Line 7, delete "(prop arac aine)." and insert -- (proparacaine). --.

In Column 20, Line 59, delete "conical" and insert -- corneal --.

In Column 21, Line 11, delete "cutaneus" and insert -- cutaneous --.

In Column 22, Line 21, delete "conical" and insert -- corneal --.

In Column 22, Line 46, delete "J C," and insert -- J. C., --.

In Column 22, Line 51, delete "Landesmaki," and insert -- Lahdesmaki, --.

In Column 23, Line 35, delete "Flt" and insert -- F11 --.

In the Claims

In Column 24, Line 66, in Claim 4, delete "has" and insert -- as --.

In Column 24, Line 66, in Claim 4, after "allergy" insert -- to --.